(12) United States Patent
Ribeiro et al.

(10) Patent No.: US 8,795,284 B2
(45) Date of Patent: Aug. 5, 2014

(54) INSTRUMENTATION FOR REPAIR OF MENISCUS TISSUE

(75) Inventors: Helio M. Ribeiro, Newark, NJ (US); Joed Canales, Harrison, NJ (US); Cesar Chavista, Rahway, NJ (US); Gregory C. Fanelli, Danville, PA (US); John E. Barker, Effort, PA (US)

(73) Assignee: Musculoskeletal Transplant Foundation, Edison, NJ (US)

(*) Notice: Subject to any disclaimer, the term of this patent is extended or adjusted under 35 U.S.C. 154(b) by 140 days.

(21) Appl. No.: 13/317,249

(22) Filed: Oct. 13, 2011

(65) Prior Publication Data

US 2013/0096680 A1    Apr. 18, 2013

(51) Int. Cl.
A61B 17/56 (2006.01)
A61B 17/16 (2006.01)
A61F 2/46 (2006.01)
A61F 2/38 (2006.01)
A61F 2/28 (2006.01)
A61B 17/17 (2006.01)
A61B 19/00 (2006.01)

(52) U.S. Cl.
CPC ............. *A61F 2/28* (2013.01); *A61B 2019/462* (2013.01); *A61B 2019/306* (2013.01); *A61B 17/1675* (2013.01); *A61F 2/4644* (2013.01); *A61B 17/1604* (2013.01); *A61F 2/3872* (2013.01); *A61B 17/1764* (2013.01)
USPC .......................................... 606/88; 623/14.12

(58) Field of Classification Search
CPC ...... A61B 17/15; A61B 17/16; A61B 17/151; A61B 17/1617; A61B 17/1604; A61B 17/157; A61B 17/1675; A61B 17/32002; A61F 2/3872
USPC .................. 606/79, 80, 84, 86 R, 87, 96, 88; 623/14.12
See application file for complete search history.

(56) References Cited

U.S. PATENT DOCUMENTS

| | | |
|---|---|---|
| 4,711,238 A | 12/1987 | Cunningham |
| 5,092,894 A | 3/1992 | Kenny |
| 5,653,714 A | 8/1997 | Dietz et al. |
| 5,868,750 A | 2/1999 | Schultz |
| 6,468,314 B2 | 10/2002 | Schwartz et al. |
| 6,699,252 B2 | 3/2004 | Farr, II et al. |
| 7,124,762 B2 | 10/2006 | Carter et al. |
| 7,364,581 B2 | 4/2008 | Michalowicz |
| 8,152,808 B2 | 4/2012 | Steiner et al. |
| 8,152,846 B2 | 4/2012 | Steiner et al. |
| 2004/0087960 A1* | 5/2004 | Kinnett ........................ 606/88 |
| 2004/0220578 A1 | 11/2004 | Bagga et al. |
| 2009/0234452 A1* | 9/2009 | Steiner et al. .............. 623/14.12 |

* cited by examiner

*Primary Examiner* — Brian Pellegrino
(74) *Attorney, Agent, or Firm* — John S. Hale; Gipple & Hale

(57) ABSTRACT

The invention is directed toward an instrumentation kit used to replace a damaged human knee joint meniscus with an allograft meniscus implant. The kit includes a workstation having a base and upright end sections with a clamping assembly is mounted on the end sections and a movable cutting guide mounted to a side wall of each end section. The tibia is then drilled with a drill to a desired depth and length and a groove is formed in the tibia with an osteotome so that the width is the same as the width of the bone base of the meniscus implant which has been trimmed in the workstation.

17 Claims, 26 Drawing Sheets

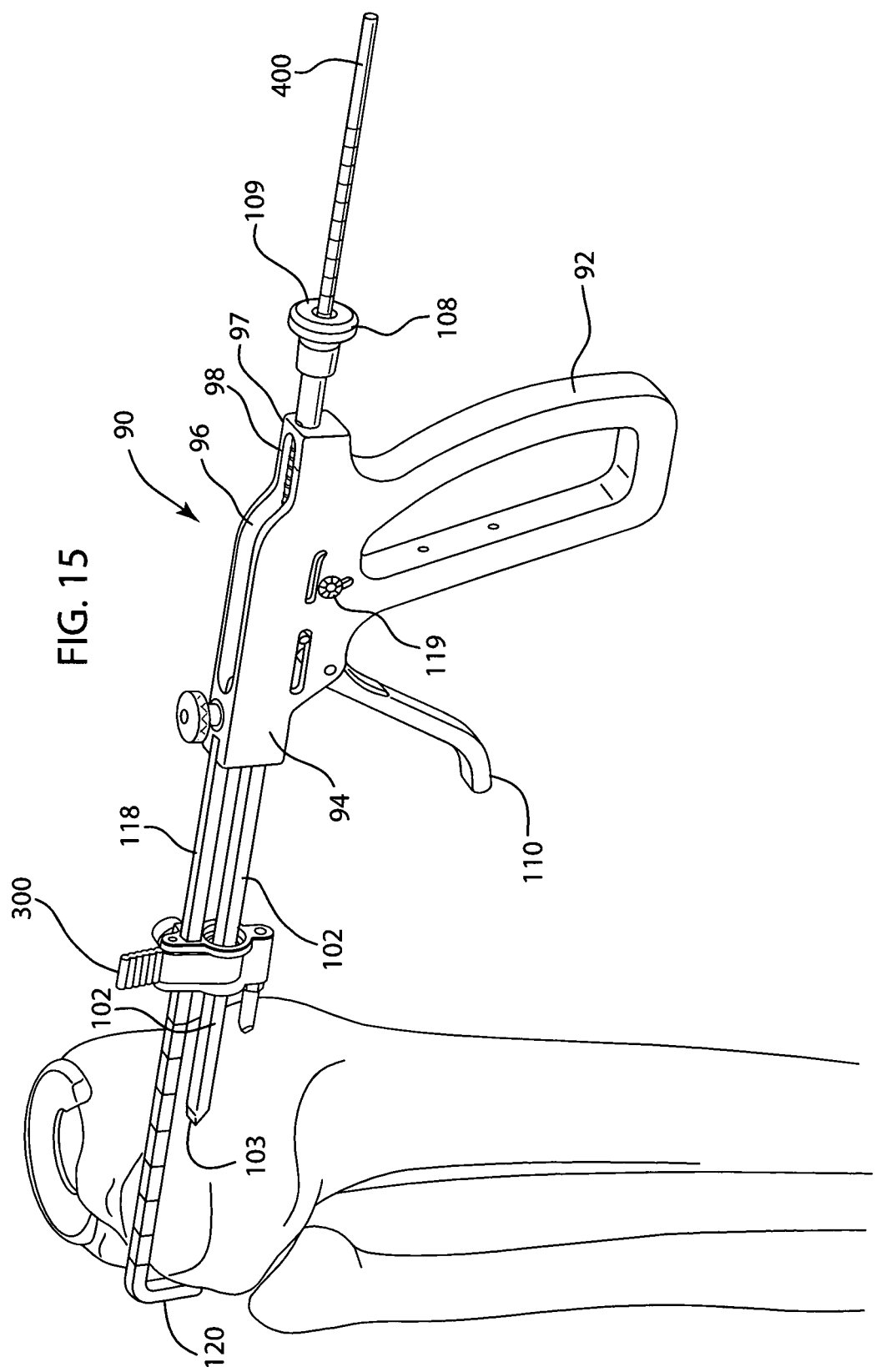

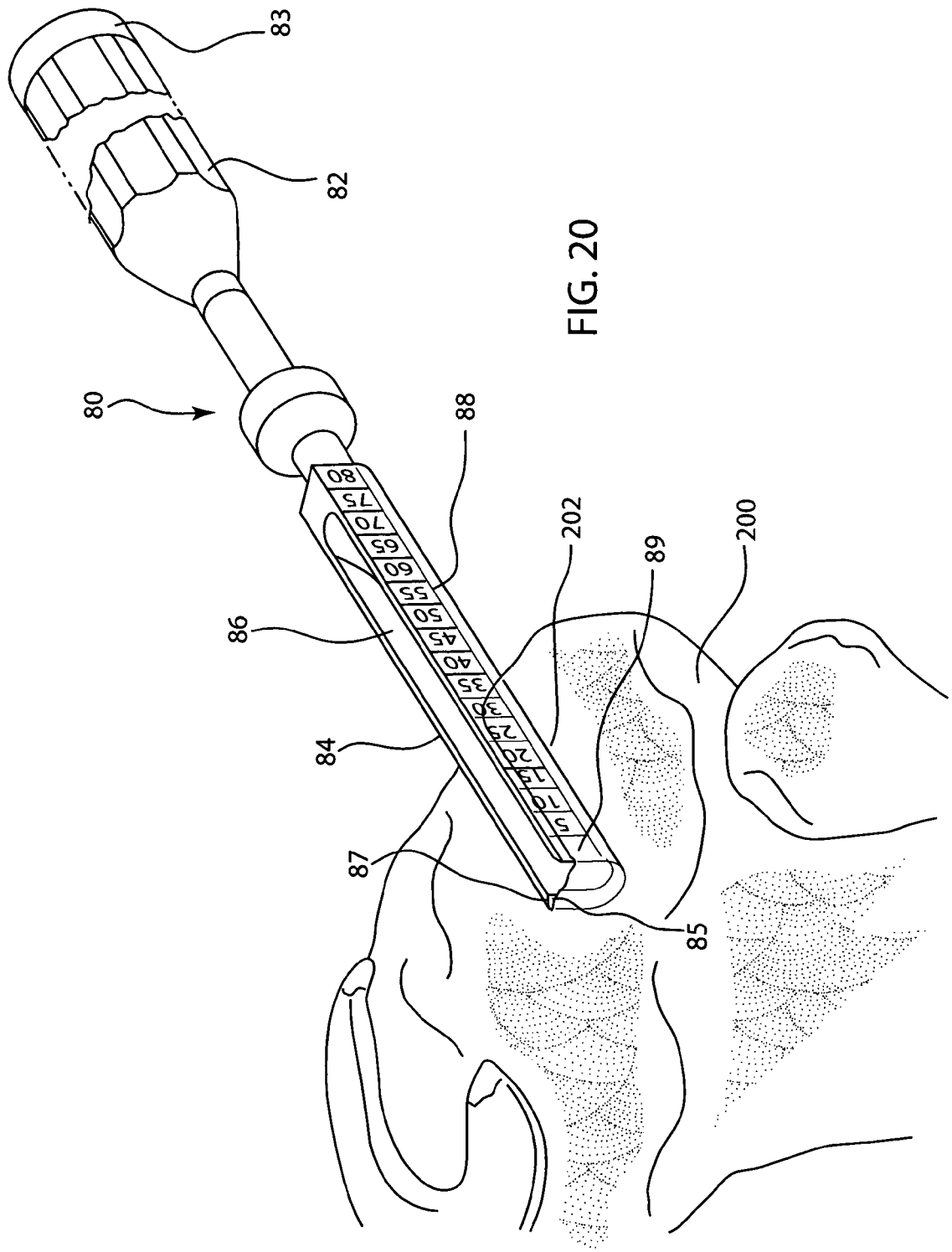

INSTRUMENTATION FOR REPAIR OF MENISCUS TISSUE

RELATED APPLICATION

None.

FIELD OF INVENTION

The present invention relates to the field of treatment of injured human knee joints, namely, to replacement and repair of a damaged human knee joint meniscus using a substantially immunologically compatible allograft meniscus.

The present invention is generally directed toward instrumentation to replace a damaged human knee joint meniscus with an allograft meniscus implant and is particularly directed toward a workstation and associated instruments for cutting and trimming the meniscus implant bone base for insertion into a groove cut into the top surface of the tibia.

BACKGROUND OF THE INVENTION

The human knee is a complex joint containing spatially interrelated bones, ligaments, and cartilaginous structures which interact to create a variety of motions. Specifically, the femoral condyles articulate with the surface plateaus of the tibia, through the cartilaginous medial and lateral menisci, and all of these structures are held in place by various ligaments.

The meniscus of the knee joint is a half moon shaped piece of cartilage that lies between the weight bearing joint surfaces of the femur and the tibia. It is triangular in cross section and is attached to the lining of the knee joint along its periphery. There are two menisci in a normal knee; the outer one is called the lateral meniscus, the inner one the medial meniscus. The menisci play an important role in absorbing impact loads.

The menisci provide stability to the knee joint. Either of the menisci may tear or split when subjected to certain forces. This injury, which is commonly referred to as torn cartilage in the knee, is painful and may limit mobility.

Undamaged menisci provide shock absorption for the knee by ensuring proper force distribution, stabilization, and lubrication for the interacting bone surfaces within the knee joint, which are routinely exposed to repeated compression loading during normal activity. Much of the shock absorbing function of the medial and lateral menisci is derived from the elastic properties inherent to cartilage. When menisci are damaged through injury, disease, or inflammation, arthritic changes occur in the knee joint, with consequent loss of function.

The meniscus, a cartilaginous tissue, performs several functions in the knee including load transmission from the femur to the tibia, stabilization in the anterior-posterior position during flexion, and joint lubrication. Damage to the meniscus results in reduced knee stability and knee locking. Over 20 years ago, meniscectomies were performed which permitted pain relief, but were subsequently found to induce the early onset of osteoarthritis.

Injury to the knee involving a tear in the meniscus is a common occurrence, often occurring in the context of athletic events, and is prevalent in the younger population. The meniscus is recognized as being vital to the biomechanical stability and protection of the knee joint. Damage to the meniscus can greatly increase the likelihood of the articular surfaces of the knee joint developing conditions such as osteoarthritis. A common remedy which has been previously used for tears in the meniscus involved removal of the meniscus. However, it has been shown that degenerative changes in the knee are directly proportional to the amount of meniscus removed. Thus, in many instances it is desirable to repair the torn meniscus with the objective being to prevent instability of the knee joint and to prevent onset of conditions such as osteoarthritis.

Of the approximately 600,000 meniscal injuries that occur annually in the United States, an estimated 80% of tears are located in the avascular, irreparable zone. Thus, instrumentation that allows repair of "non-repairable" tears by replacement of the damaged meniscus with an allograft implant would be valuable for painless musculoskeletal movement and prevention of the early onset of osteoarthritis in a large segment of the population.

Various repairs and replacements have been used to relieve pain and restore function to the joint where the cartilage has been damaged. For example hyaline cartilage may be damaged by impact injuries or worn down in the course of arthritis. Typically, the ends of the bones forming a joint are cut away and replaced with prosthetic bearings made of metal and plastic to restore pain free articulation of the joint. In cases where the damage occurs as a small localized defect, some investigators have attempted to replace only the small defect by placing a patch of replacement material, either natural or synthetic, at the defect.

Current methods for repairing tears in the meniscus are technically very challenging for the surgeon. One widely used technique requires that a long needle with a suture be passed through the torn meniscus and the knee joint. The needle carrying the suture is passed through the meniscus and the knee in its entirety several times until the meniscal tear is closed. As this procedure is typically performed arthroscopically, the amount of space available within the knee for manipulating the long needle through the meniscus is extremely limited. The procedure often requires more than one pair of hands, with one pair inserting the needle into the knee while another pair uses graspers, operating in the limited inflated space in the interior of the knee, to shuttle the needle through the meniscus and out the other side of the knee.

One area of meniscal repair is the use of allograft meniscal tissue used as an implant replacement for the damaged meniscus. U.S. Pat. No. 7,124,762 issued Oct. 24, 2006 discloses a meniscus allograft with an integral bone bridge and is directed toward a meniscus having a bone block with a trapezoidal shape in cross section which is mounted to a dovetail groove cut in the tibia. The meniscus is mounted in a graft workstation having movable opposing clamp arms and the block is then marked, cut and trimmed by a saw. The bone bridge is held in a clamp and trimmed with a surgical saw so that it fits into a trapezoidal shaped or dovetail shaped blind end groove cut into the upper surface of the tibia. A rasp is used to create the orthogonal angle of the dovetail transplant. This type of meniscal allograft transplant is currently being used by Arthrex, Inc.

A similar allograft implant having a rectangular bone bridge is trimmed on a cutting board so that the bridge fits into a rectangular groove cut into the tibial surface. This type of meniscal allograft transplant is currently being used by the Stryker Corporation. The tibular surface is lined and a hole is drilled parallel to the marker line with a rectangular groove in the tibular surface being formed by a rasp. The allograft implant and instruments and method of transplantation are shown in U.S. Pat. No. 6,699,252 issued Mar. 2, 2004.

A double bone plug meniscus surgical technique is utilized by Cryolife, Inc. with cylindrical bone plugs cut on each end of the horns of the allograft meniscus, the horns being placed in cylindrical blind bores cut into the tibial surface, and held in place by sutures. Another reference of interest is U.S. Pat.

No. 5,092,894 issued Mar. 3, 1992 which discloses a biocompatible meniscus implant constructed of deformable and resilient material with the horns of the meniscus being mounted in tubing which is inserted into cylindrical bores cut into the tibia.

U.S. Patent Publication Number 2008/0183291 published Jul. 31, 2008 is directed toward a tongue and groove method of fixing a meniscus implant to a horizontal channel cut across the surface of a tibial plateau. In one embodiment, the tongue or keel for the implant is formed of a polymer material which adheres to a metal lattice constructed within the intermediate position.

U.S. Pat. No. 6,468,314 issued Oct. 22, 2002 is a complex cartilage repair system for forming and inserting a plug in a cartilage surface to repair destroyed articular cartilage.

Meniscal cutting devices have also been disclosed in U.S. Pat. No. 4,711,238 issued Dec. 8, 1987.

There is, thus, a need for a simplified procedure to trim a meniscus transplant and prepare the tibial surface to receive the transplant along with instrumentation for conducting this procedure.

SUMMARY OF THE INVENTION

The present invention provides a substantially non-immunogenic meniscal cartilage allograft implant for implantation into a human in need of knee meniscus repair and an instrument kit for the surgeon to accomplish the implant. In particular, the instrument kit includes a workstation which secures the meniscus implant in a fixed position and allows maximum flexibility for cutting the implant to the required dimensions.

The present invention is directed to an instrumentation kit for trimming a meniscus allograft implant and instrumentation to surgically replace a damaged human knee joint meniscus with an allograft meniscus.

It is also an object of the invention to provide a pre-machined allograft meniscus implant having a bone base connecting the horns of the meniscus which can be mounted and fastened to a tibial surface.

It is yet another object of the invention to provide an implant cutting and trimming workstation which allows the surgeon to cut and trim the implant to the desired dimensional criteria which is optimum to the individual patient.

It is yet another object of the invention to provide a drill for actually drilling a tibia a predetermined distance so that a uniform tibia groove can be formed across the surface of the tibia.

It is still another object of the invention to provide an osteotome for uniformingly cutting a groove across the surface of the tibia.

These and other objects, advantages, and novel features of the present invention will become apparent when considered with the teachings contained in the detailed disclosure which along with the accompanying drawings constitute a part of this specification and illustrate embodiments of the invention which together with the description serve to explain the principles of the invention.

BRIEF DESCRIPTION OF THE DRAWING

FIG. 15 is side perspective view of a tissue clamping drill mounted on a tibia being prepared for the meniscus implant;

FIG. 20 is an enlarged top perspective view of the osteotome with measuring indicia entering the upper surface of the tibia to cut an implant groove;

DETAILED DESCRIPTION OF THE INVENTION

The preferred embodiment and best mode of the present invention is shown in FIGS. 10 through 21.

Figure 24:
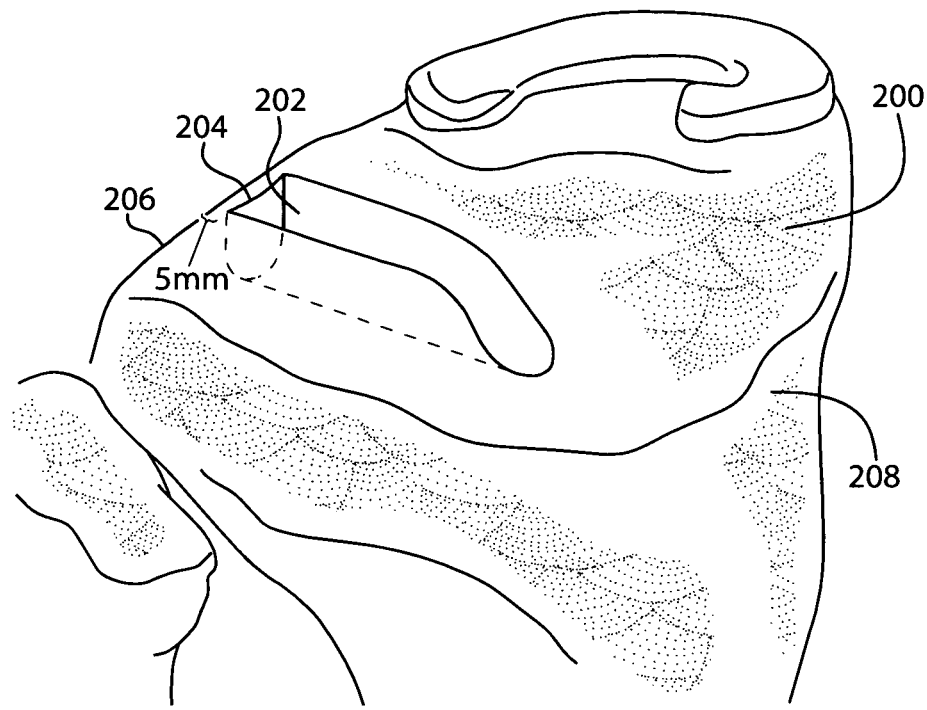
FIG. 24 is a perspective view of the tibia showing a chiselled groove on the top surface of the tibia.
Figure 25:
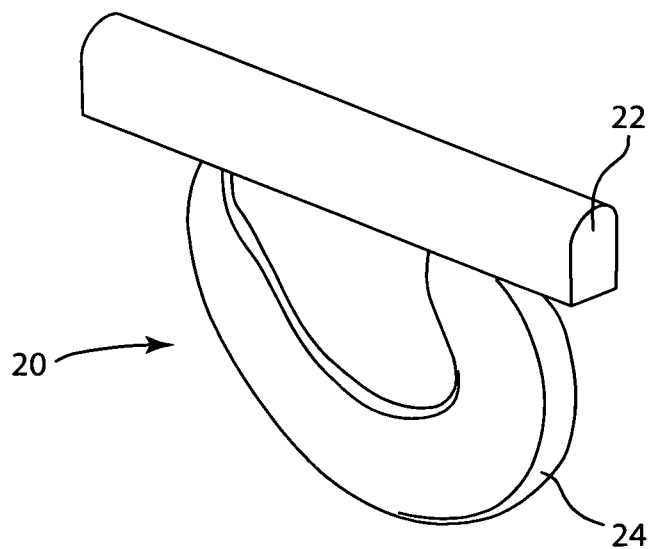
FIG. 25 is a perspective view of a finished allograft meniscus implant.

In the drawings, an allograft meniscus implant 20 with a bone base 22 and meniscus 24 is shown. The implant bone base 22 after having been cut, trimmed and measured as shown in FIG. 25, is mounted in groove 202 of tibia 200 shown in FIG. 24.

The feature of the bone base 22 of the implant that makes it desirable as a surgical material is its ability to slowly resorb and be integrated into the groove space on the tibia it occupies while allowing the bodies own healing mechanism to restore the repairing bone to its natural shape and function by a mechanism known in the art as creeping substitution.

The allograft meniscus implant 20 is prepared with the use of an instrument kit comprising a cutter workstation assembly 30 which allows the meniscus implant base 22 to be cut, trimmed and sized, a rasp assembly 70, an osteotome or tissue chisel 80 and a clamping drill 90.

Figure 9:
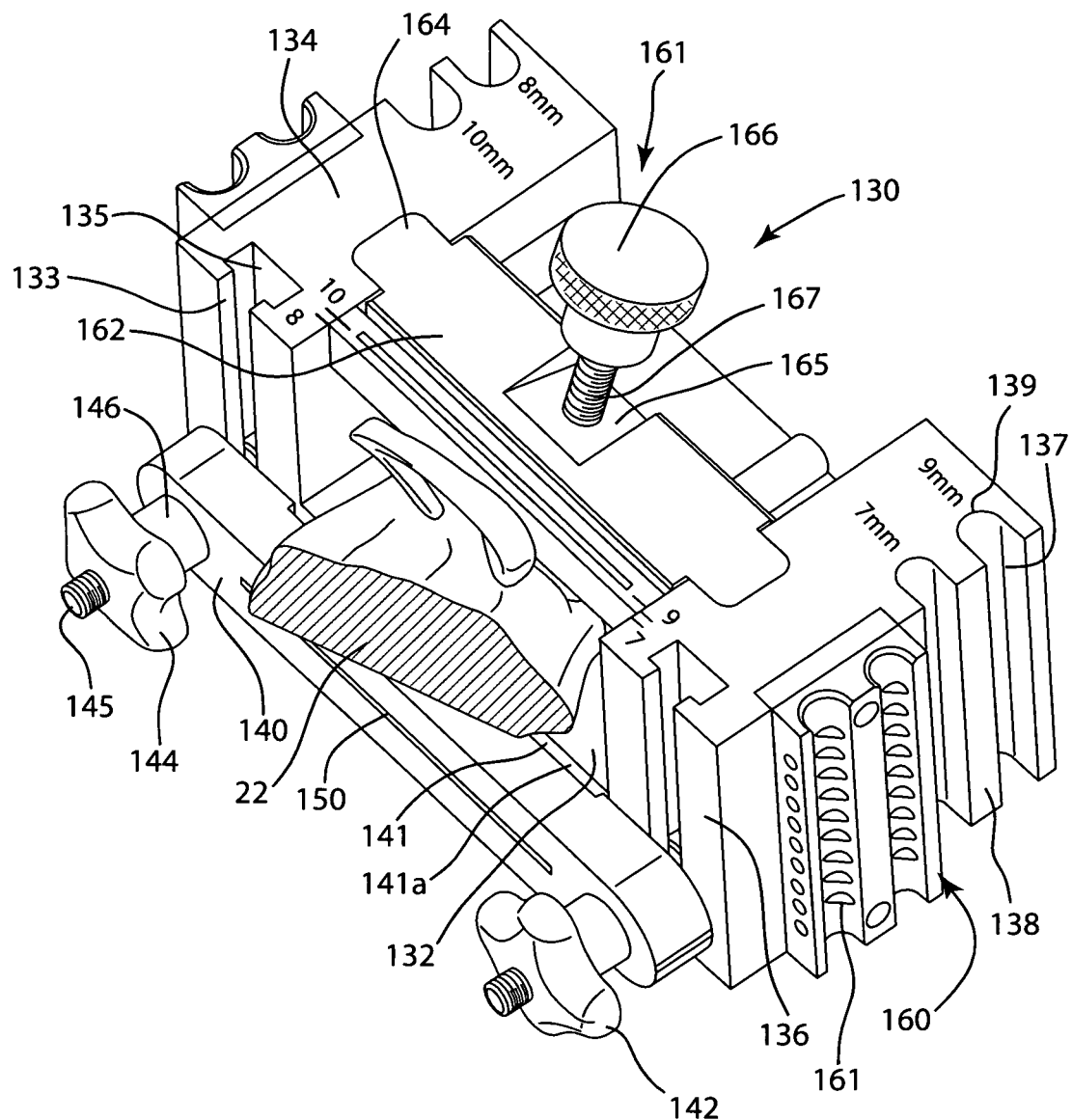
FIG. 9 is a perspective view of an alternate embodiment of the meniscus cutting workstation with an angled clamp bar and rasp attachment.

An implant cutting workstation 30 as shown in FIGS. 1-8 is constructed with a stainless steel block "U" shaped integrally formed housing 31 having a base section 32 and upstanding end sections 34. The housing 31 is constructed of rectangular sections with planar surfaces so that the housing can be stood on either end, the base, the top, or the sides allowing the surgeon maximum latitude in cutting and trimming the implant. Each end section 34 defines a "T" shaped groove 35 cut in its side wall 36 and a plurality of implant base sizing grooves 37 which are cut into and run parallel to each other on its end wall 38. The sizing grooves 37 have different widths ranging from 7 mm to 10 mm with a rounded base 39. If desired, one of the sizing grooves can be replaced with a rasp groove which is used to round the bottom of the trimmed base of the implant. It is of course noted that greater or lesser groove widths can formed in the end wall 38 as desired. Representative groove widths are shown in FIG. 9. If desired, marking indicia can be etched, painted or cut on the end section top planar face surface of each end section to allow the user to ascertain the width of the base 22 of the implant 20 so that the same can be accurately placed in a seating groove 202 cut into the tibia 200 shown in FIG. 24.

Figure 1:
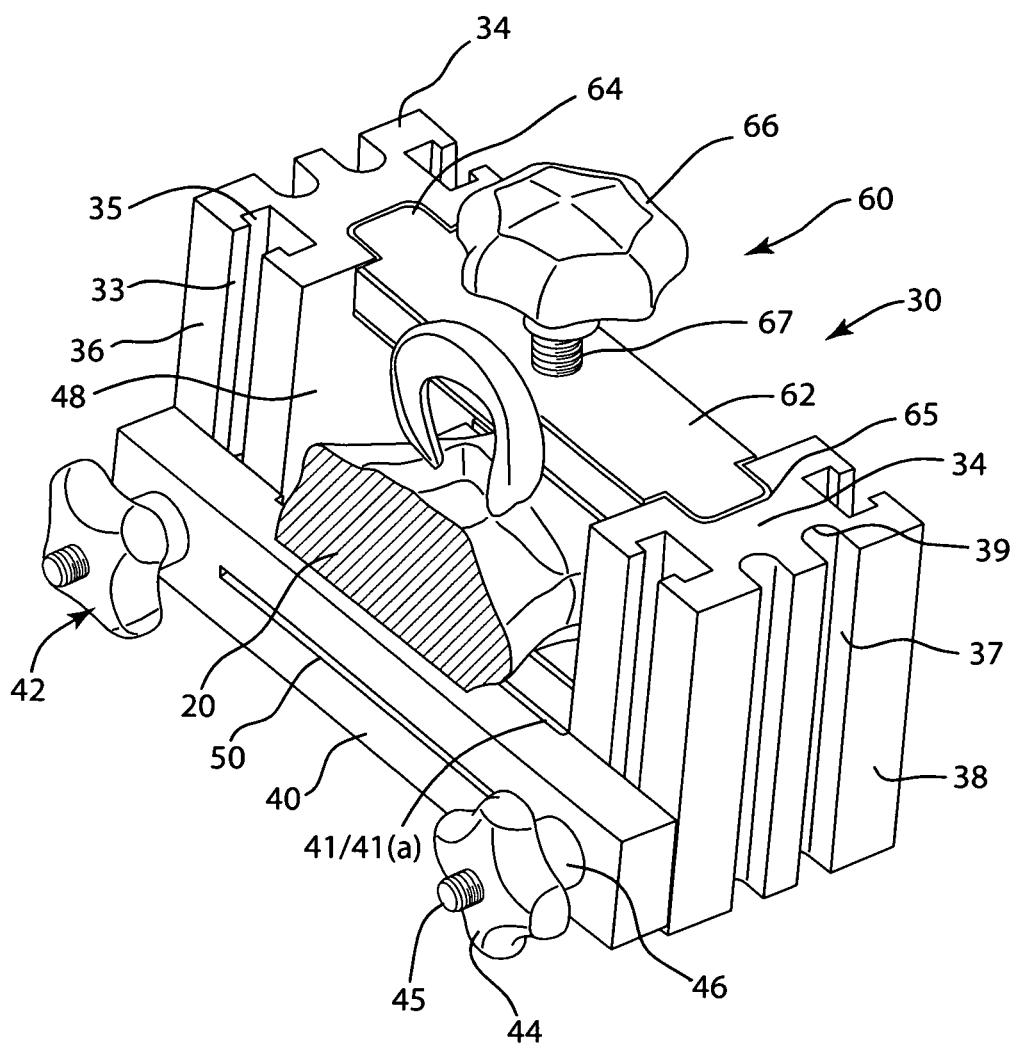
FIG. 1 is a perspective view of a meniscus implant cutting workstation with an allograft meniscus implant mounted therein.
Figure 2:
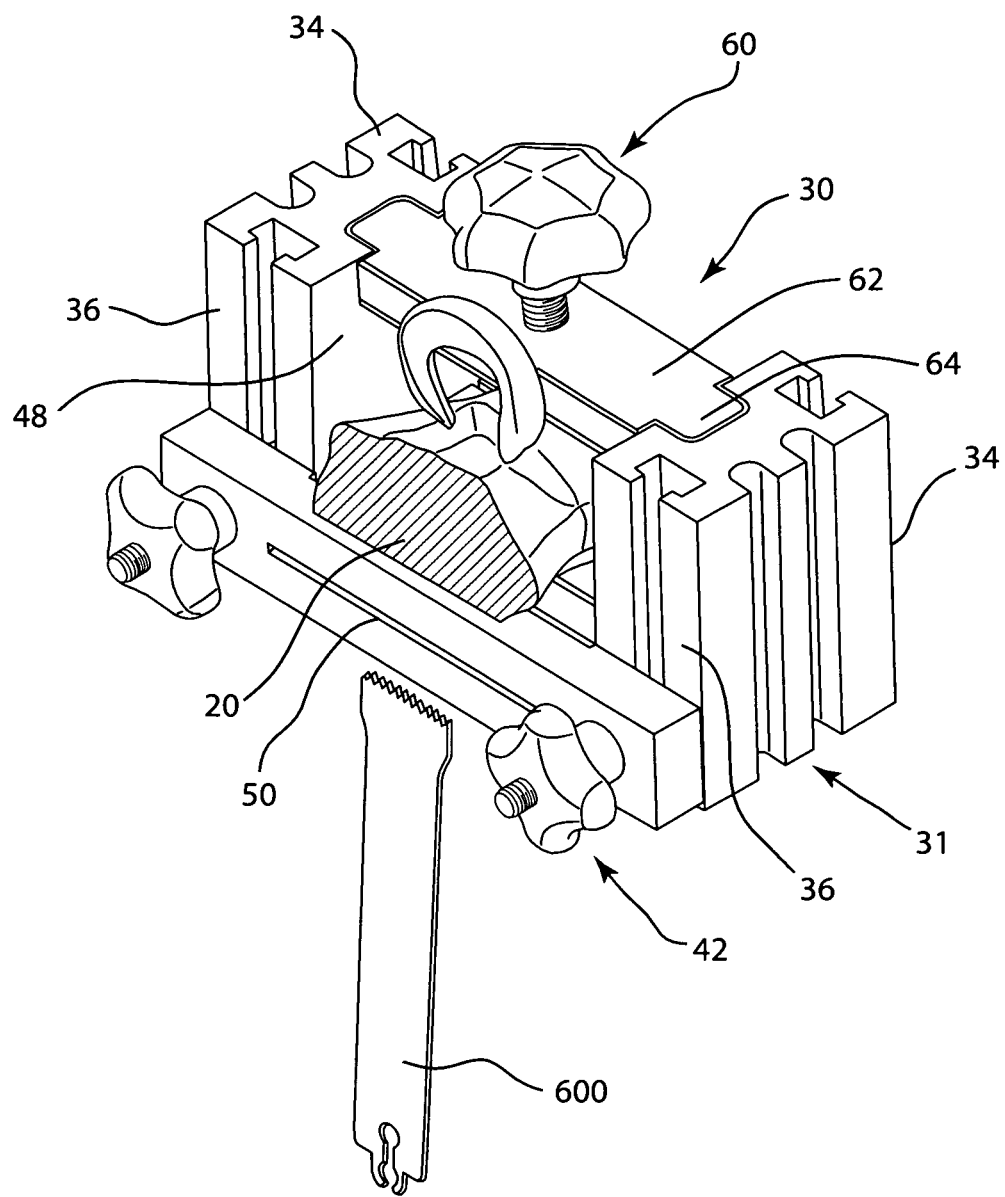
FIG. 2 is a perspective view of the meniscus implant cutting workstation of FIG. 1 showing a saggital saw about to be inserted into the cutting guide bar recess slit for vertically cutting a meniscus transplant base.
Figure 3:
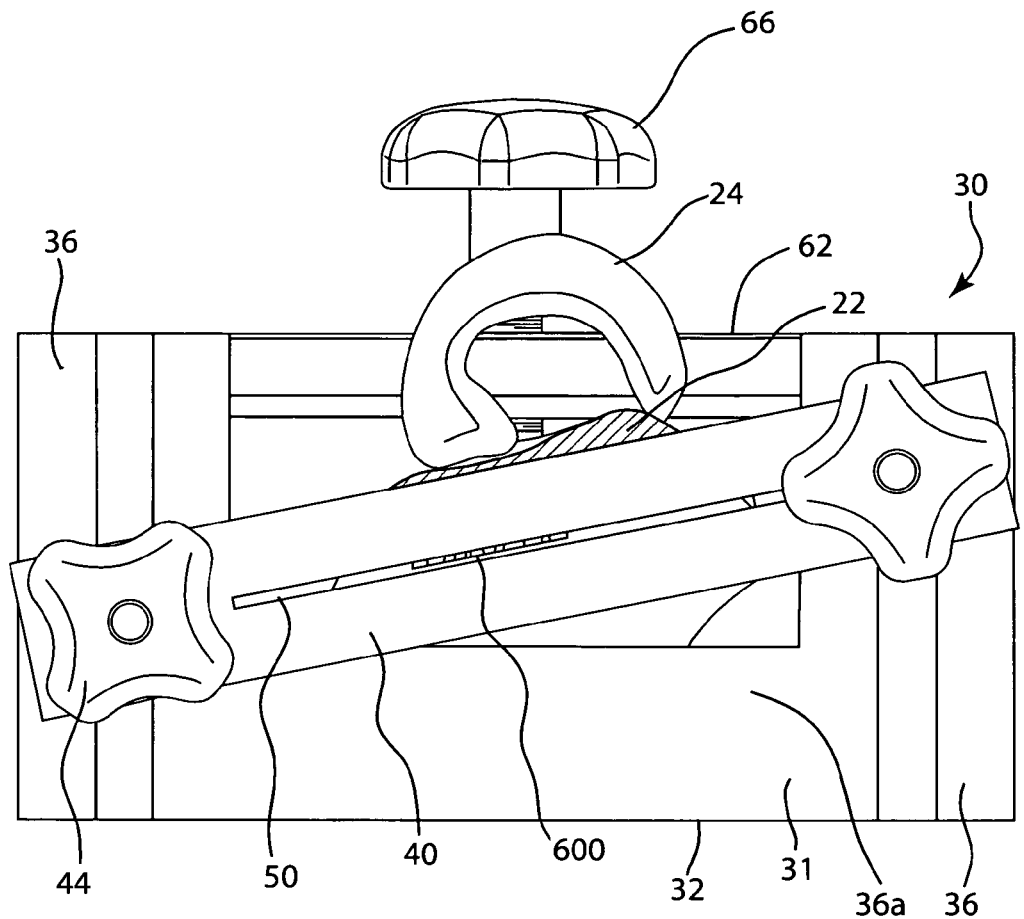
FIG. 3 is an enlarged side view of the cutting workstation of FIG. 1 showing the cutting guide bar positioned at an angle and a saggital saw inserted into the cutting guide bar longitudinal slit.
Figure 4:
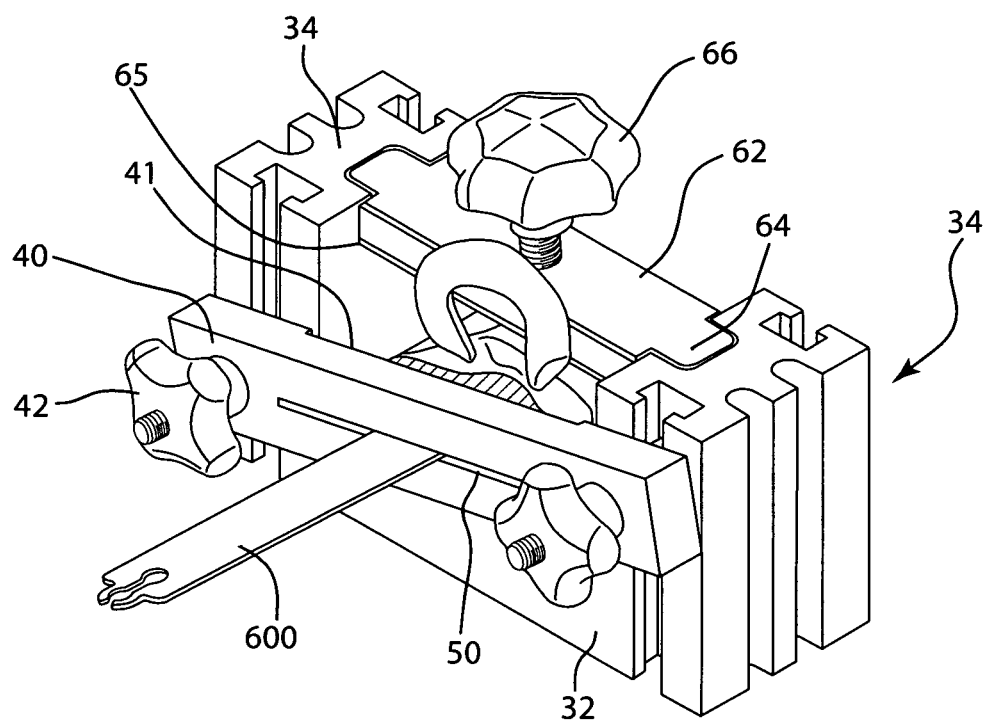
FIG. 4 is a perspective view of the meniscus cutting workstation of FIG. 3 with an allograft meniscus implant mounted therein and a saggital saw inserted for angular cutting of the meniscus implant base.
Figure 5:
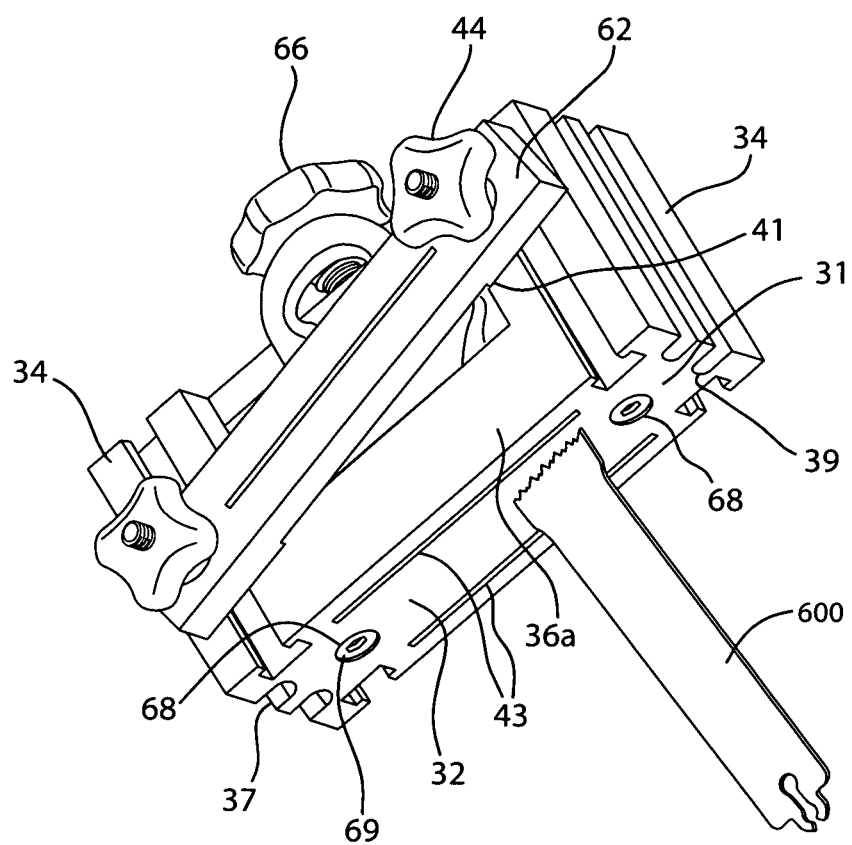
FIG. 5 is a bottom perspective view of the meniscus cutting workstation of FIG. 4 with a saggital saw positioned below the base of the workstation.
Figure 6:
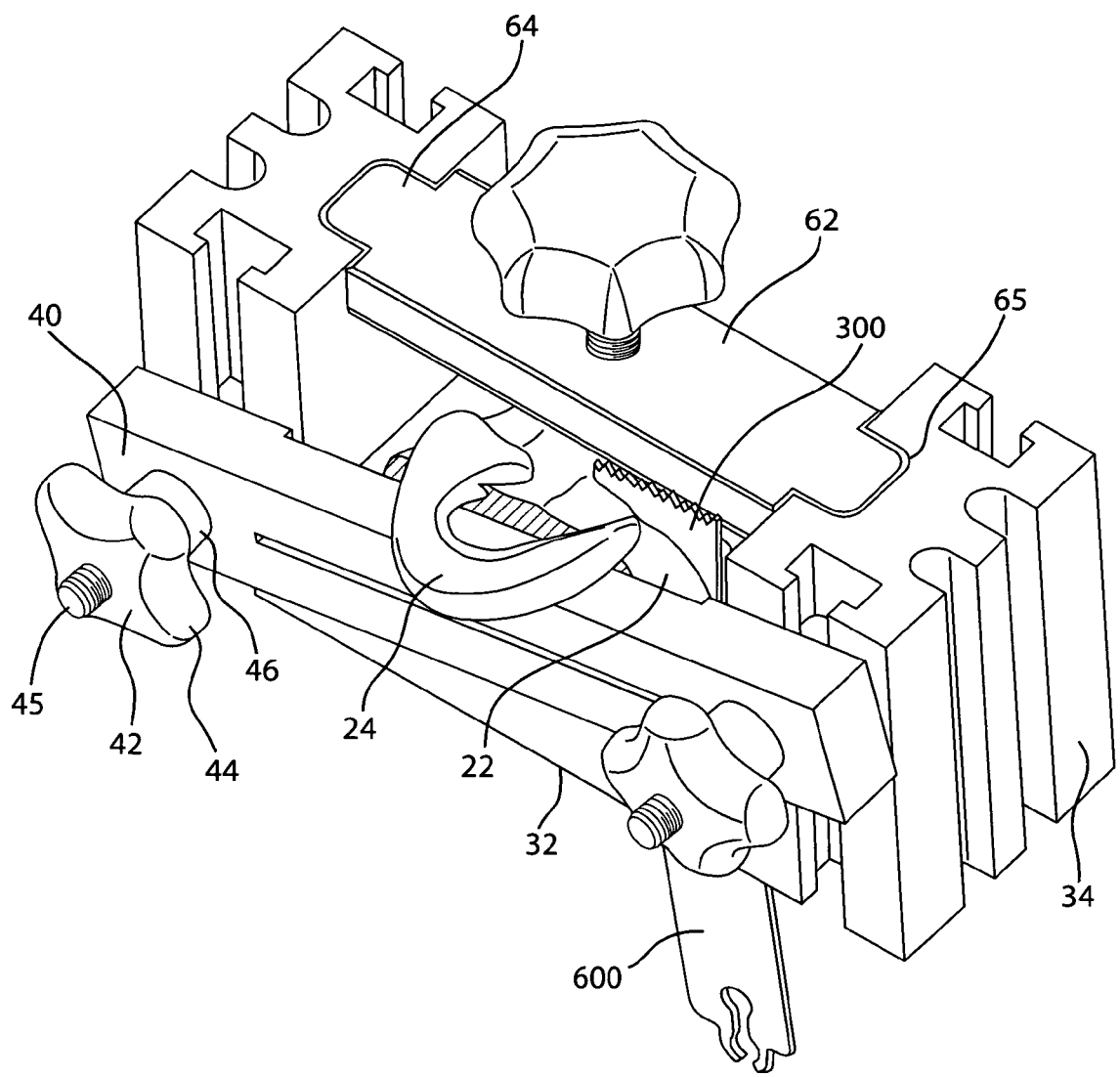
FIG. 6 an enlarged reversed enlarged perspective view of the meniscus cutting workstation of FIG. 5 with an allograft meniscus implant mounted therein and a saggital saw vertically cutting the base of the implant.
Figure 7:
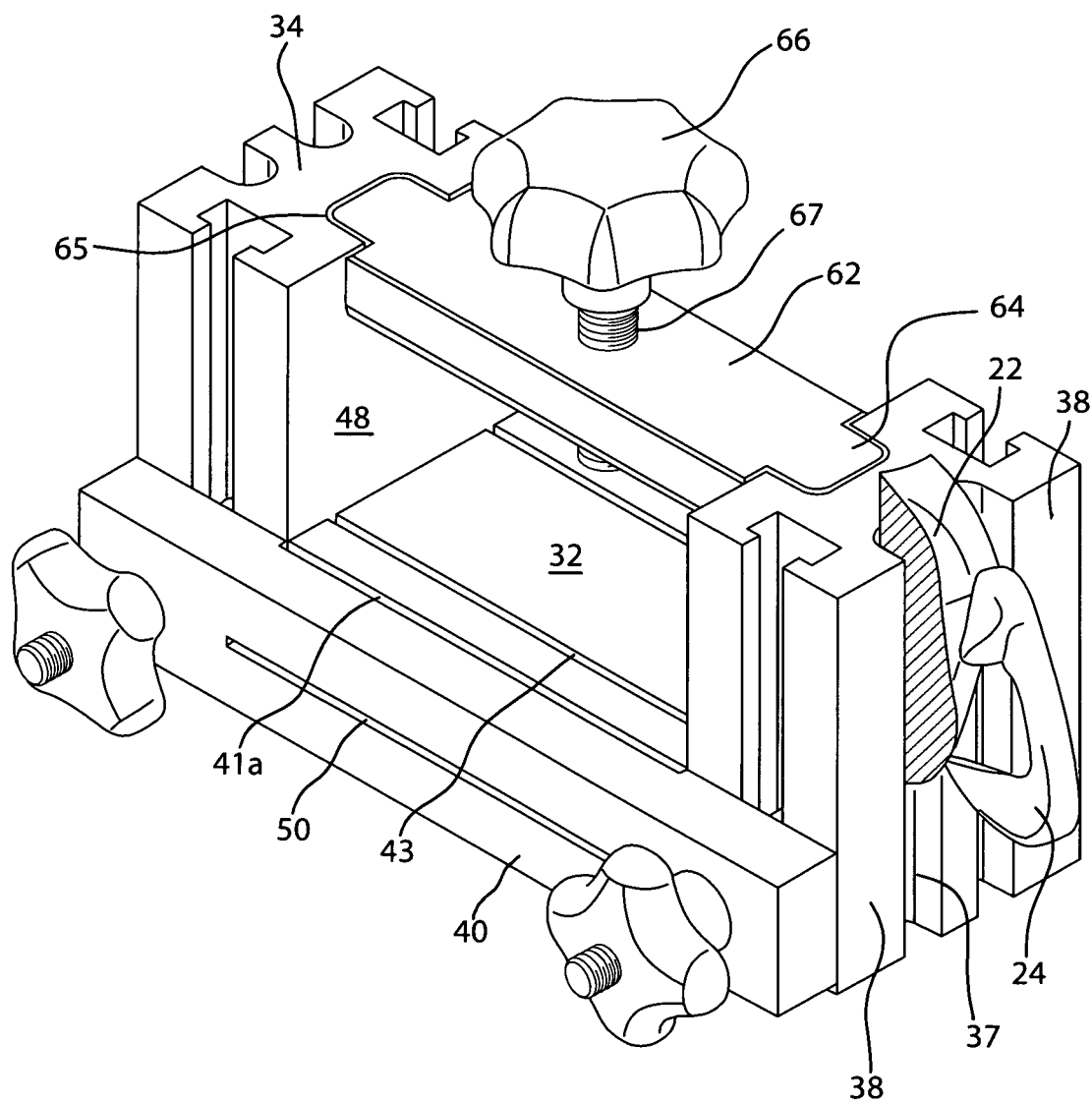
FIG. 7 is a perspective view of the meniscus cutting workstation of FIG. 1 with the allograft meniscus implant base being measured in a sizing groove.
Figure 8:
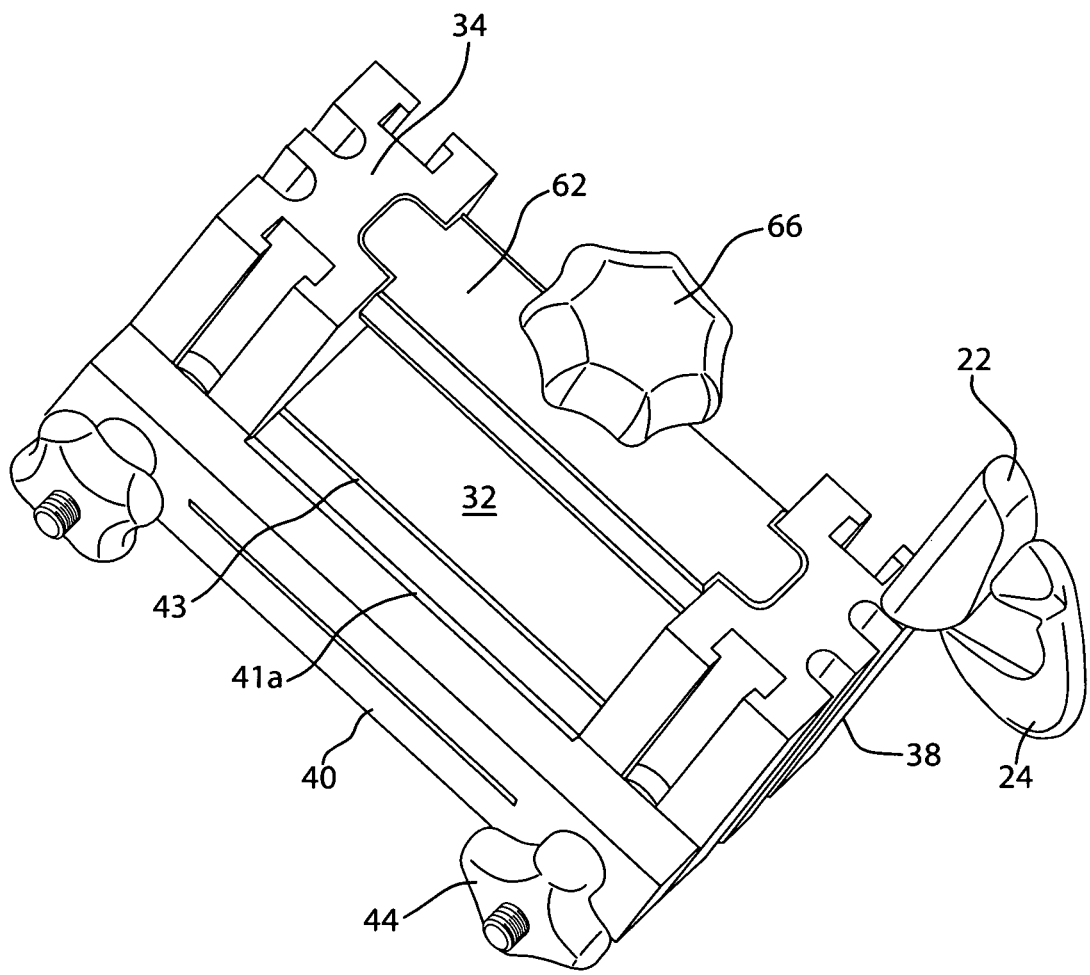
FIG. 8 is a top perspective view of the meniscus cutting workstation of FIG. 1 with an allograft meniscus implant removed from a sizing groove.

A slideable angularly adjustable planar surfaced cutting guide bar 40 is mounted in the "T" shaped grooves 35 through the usage of two thumb screw assemblies 42. Each assembly 42 has a handle 44 with an extended boss 46 threadably mounted on a threaded shank 45 which extends through throughgoing bores (not shown) cut in each end of cutting guide bar 40. The threaded shank 45 has a circular coin shaped base (not shown) of greater diameter than the width of the entry opening 33 of groove 35 and is mounted in the widest portion of groove 35. The securing handle 44 is threadably mounted on the threaded shank 45 to hold the cutting guide bar 40 in a fixed position against the planar side wall 36 of each end section 34. The cutting guide bar 40 also defines a centrally positioned straight line through going slit 50 which extends through the cutting guide bar allowing horizontal or angular cuts to be made to the implant base 22. As seen in FIG. 3, the surface of the meniscus implant 20 has to slope generally in the range of about 5° to about 10° to match the slope of the tibia 200 so a corresponding angular cut has to be made in the base of the implant. The side of the cutting guide bar 40 as shown in FIG. 1 is provided with a side recess 41 which together with the side wall 36(a) of the base section 32 forms a linear slit 41(a) which is oriented perpendicular to slit 50, allowing vertical cuts to be made in the implant 20. The base 32 also defines a plurality of parallel through going linear slits 43 as shown in FIG. 5 which are parallel to linear slit 41(a) allowing a number of cutting positions for the saggital saw blade 600. The plurality of parallel aligned cutting slits (41(a), 43) are adapted to receive a saggital saw blade 600 of standard construction as shown in FIGS. 4 and 5 to trim the meniscus bone base 22 to a desired width to fit into groove 202 cut into the tibia 200. As shown in FIG. 5, the workstation base 32 has threaded bores 68 cut in opposite ends allowing fasteners 69 such as metal screws to engage threaded blind bores formed in the clamp support bar tab ends 64 thereby holding the support bar 62 fixedly in place in seats 65. A clamp screw assembly 60 for the implant is mounted and secured to the support bar 62. The clamp screw assembly comprises a handle 66 having a threaded shaft secured thereto and extending therefrom and a clamp support bar 62. The clamp support bar 62 has shaped tab ends 64 which are mounted in corresponding shaped recess seats 65 cut in the inner sidewall surface 48 of each end section 34 and are held in place by metal screws 69 which are mounted through bores 68 which lead from the base of base section 32 to the bottom of the recess seats 65 cut into the top portion of end sections 34. The distal end of the screw 69 is threaded and engages a threaded blind bore cut in tab ends 64 to hold the clamp support bar 62 securely in place. Thus, the clamp bar 62 is securely mounted to the end sections 34. A threaded thumb screw is mounted to the clamp bar 62 in a threaded through going bore and is adapted to rotate in the clamp bar 62 so that the distal end of the thumb screw shank 67 engages the bone base of the implant 20 holding the same in a secured position in the workstation 30.

Another preferred embodiment of the cutting workstation 130 is shown in FIG. 9. In this embodiment, the workstation 130 is a stainless steel "U" shaped integrally formed housing having a planar base section 132 and upstanding generally rectangular shaped end sections 134. Each end section 134 defines a "T" shaped groove 135 cut in its side wall 136 and defines a plurality of sizing grooves 137 which run parallel on its end wall 138. The sizing grooves 137 are parallel to each other and have different widths ranging from 7 mm to 10 mm and are formed with a rounded base 139. It is of course noted that greater or lesser groove widths can formed in the end wall 138 as desired. If desired, marking indicia can be etched, painted or cut on the end section top planar face surface as shown in to allow the user to ascertain the width of the base 22 of the implant 20 so that the same can be seated in groove 202 cut into the tibia 200 shown in FIG. 24. This embodiment also has a rasp assembly 160 having a rounded bottom cutting surface 161 which can be used to trim the bottom of the base 22 of the implant to fit into tibial groove 202.

A slideable angularly adjustable planar surfaced cutting guide bar 140 is mounted in grooves 135 through the usage of two thumb screws 142 which have a handle 144 with an extended boss 146 threadably mounted to a threaded shank 145 which extends through throughgoing bores (not shown) cut in each end of cutting guide bar 140. The threaded shank 145 has a circular coin shaped base (not shown) of greater diameter than groove entry opening 133 and the coin shaped base is mounted in groove 135. Each handle 144 is threadably mounted on the threaded shank 145 to hold the cutting guide bar 140 in a fixed position against the planar side wall 136 of the end section 134. The cutting guide bar 140 also defines a centrally positioned straight line slit 150 which extends through the cutting guide bar allowing linear cuts to be made on the implant. The interior side of the cutting guide bar 140 is provided with a side recess 141 which together with the side wall of the base section 132 forms a linear slit 141(a) positioned perpendicular to slit 150, allowing vertical cuts to be made in the implant. The base section 132 also defines a plurality of through going parallel linear slits as shown in FIG. 5 which are parallel to linear slit 141(a) allowing a number of cutting positions. The plurality of parallel aligned cutting slits are adapted to receive a saggital saw blade of standard construction as to trim the meniscus bone base 22 to a desired size to fit into a groove 202 cut into the tibia 200. A clamp screw assembly 161 is mounted and secured to the inner side wall surface of the end sections 134. A clamp support bar 162 has shaped tab ends 164 which are mounted in recess seats cut into the top surfaces of the end sections 134. The base 132 has bores as shown in FIG. 5 cut in opposite ends, allowing fasteners mounted in the bores to threadably engage threaded blind bore tab ends 164 of the clamp support bar 162. The clamp support bar 162 has an inclined central recess 165 which allow the thumb screw 166 to be angled. The threaded thumb screw 166 is mounted in a threaded through going bore in the clamp bar 162 and is adapted to rotate in the clamp bar 162 so that the distal end of the thumb screw shank 167 engages the bone base 22 of the implant 20 holding the same in a secured position in the workstation 130.

Figure 10:
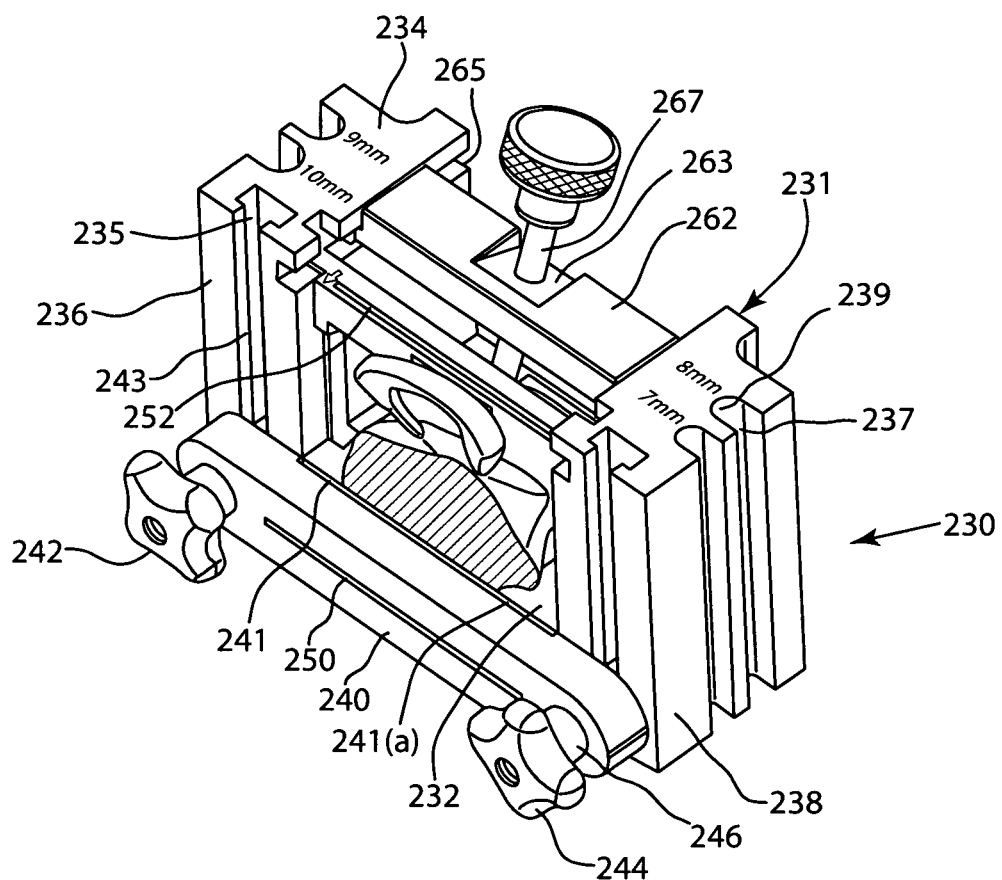
FIG. 10 is a perspective view of the preferred embodiment of the meniscus implant cutting workstation with a drop in cutting guide insert.

The most preferred workstation embodiment is cutting workstation 230 as shown in FIGS. 10-13. Cutting workstation 230 is constructed with a stainless steel block "U" shaped integrally formed housing 231 having a base section 232 and upstanding end sections 234. Each end section 234 defines a "T" shaped groove 235 cut in its side wall 236 and defines a plurality of implant base sizing grooves 237 which run parallel to each other on its end wall 238. The sizing grooves 237 have different widths ranging from 7 mm to 10 mm as shown in FIG. 10 with the grooves being formed with a rounded base 239. It is of course noted that greater or lesser groove widths can formed in the end wall as desired. If desired, marking indicia can be etched, painted or cut on the end section top planar face surface to allow the user to ascertain the width of the base of the implant 20 so that the same can be placed in the seating groove 202 cut into the tibia 200 shown in FIG. 24.

A slideable angularly adjustable cutting bar 240 is mounted in grooves 235 through the use of two thumb screws 242 which have a head 244 with an extended boss 246 mounted on a threaded shank (not shown). Each threaded shank extends through throughgoing bores (not shown) cut in each end of cutting bar 240. The threaded shank has a head of greater diameter than the width of the entry opening 243 of groove 235 and is mounted in the widest portion of groove 235. The securing handle 244 is threadably mounted on the threaded shank to hold the cutting bar 240 in a fixed position against the side wall 236 of each end section 234. The cutting bar 240 also defines a centrally positioned straight line slit 250 which extends through the cutting bar allowing horizontal cuts to be made in the implant. The interior side of the cutting bar 240 is provided with a side recess 241 which together with the side wall of the base section forms a linear slit 241(a) which is perpendicular to slit 250, allowing vertical cuts to be made in the implant 20.

Figure 11:
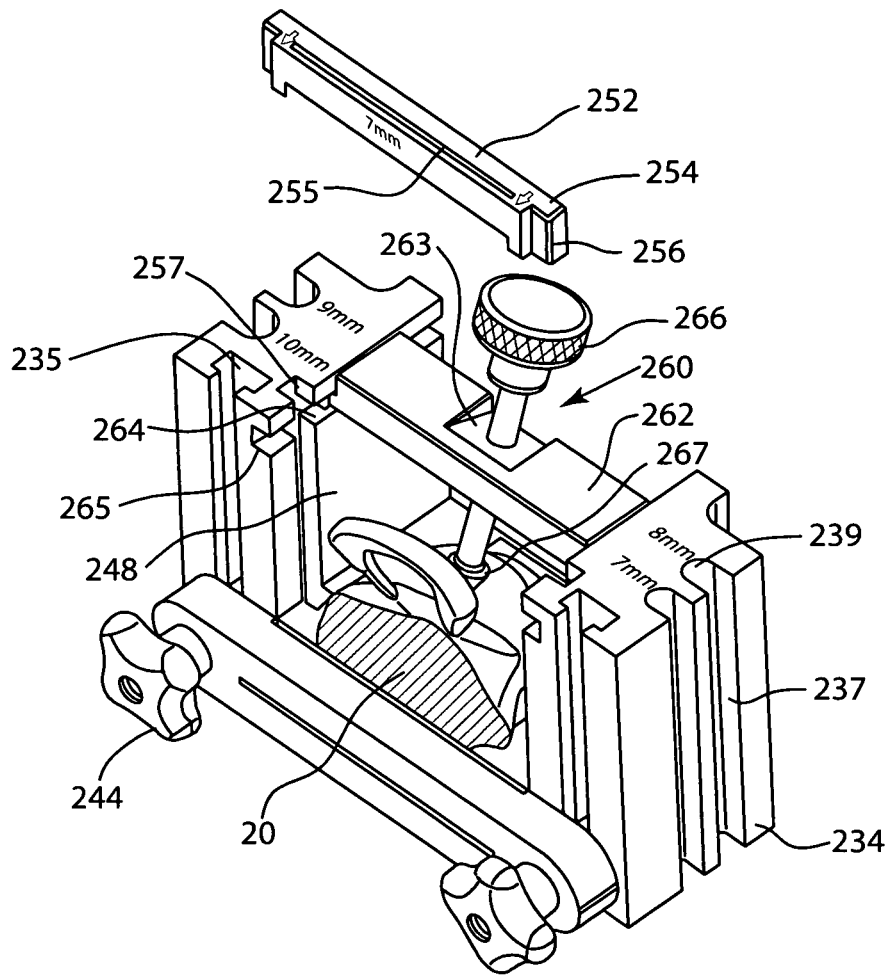
FIG. 11 is another perspective view of the preferred embodiment of the meniscus implant cutting workstation of FIG. 10 with a drop in cutting guide insert shown in exploded view.

Drop in inserts 252 as shown in FIGS. 10 and 11 of differing sizes can be used in the workstation 230. Each drop in insert comprises a bar member 254 defining a longitudinal through going slit 255 and end sections 256 which fit into the rectangular shaped top grooves 257 cut in the inner side walls 248 of end sections 234. Each drop-in insert is marked with a width measurement allowing the surgeon to cut the base 22 of the implant to the desired width as the implant is held in a fixed position within the workstation with one side of the base having been previously cut along slit 241(a). The drop-in insert is inserted over meniscus cut graft for vertical top cutting of the base 22.

A clamp screw assembly 260 is mounted to each end section 234. The clamp screw assembly 260 comprises a clamp support bar 262 with rectangular shaped ends 264 of reduced depth which are mounted in corresponding shaped grooves 265 cut in the inner sidewall surface 248 of each end section 234. The central portion of bar 262 has an inclined cutout 263 with a throughgoing bore centrally positioned in the cutout 263. The shank of the thumb screw is mounted in the cutout threaded through going bore and is adapted to rotate in the clamp bar 262 so that the distal end 267 of the thumb screw shank, which is preferably a swivel clamp, engages the bone base 22 of the implant 20 holding the same in a secured position in the workstation 230.

Figure 12:
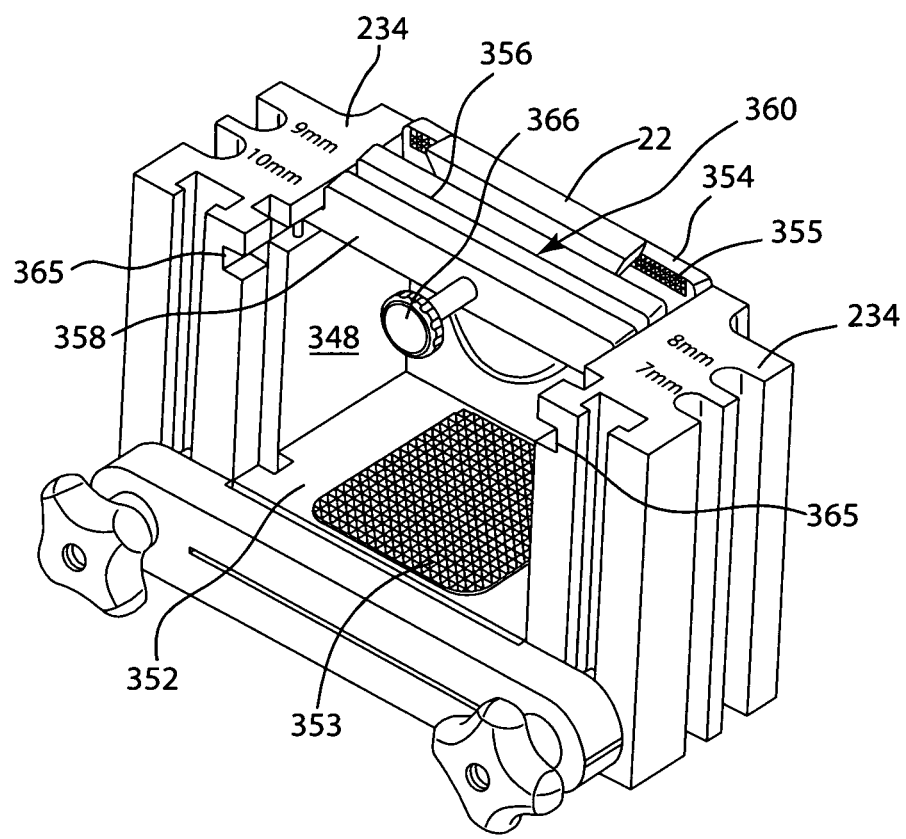
FIG. 12 is a perspective view of the preferred embodiment of the meniscus implant cutting workstation of FIG. 10 with the clamping cross bar removed using a drop in securing assembly mounted on the workstation.
Figure 13:
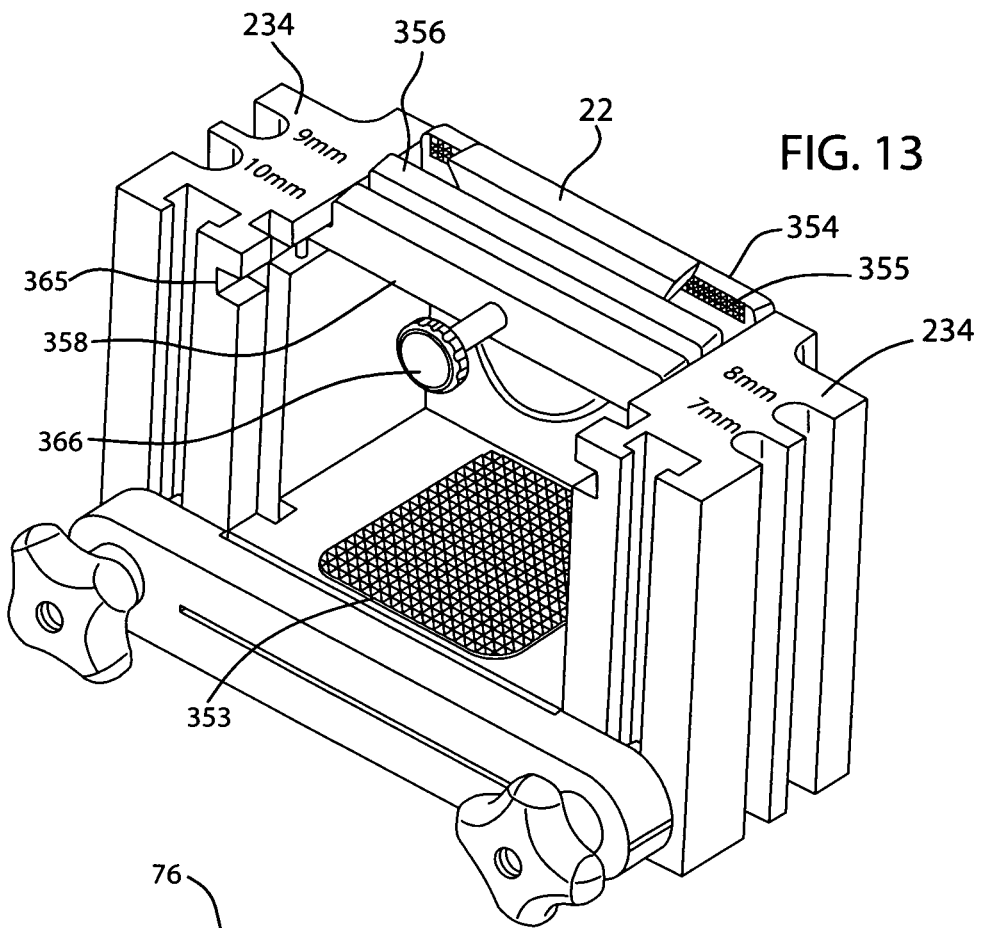
FIG. 13 is a perspective view of the workstation of FIG. 12 showing the meniscus graft rasp placed on the base of the implant.

An alternate clamping device for the workstation 230 is shown in FIGS. 12 and 13. This workstation is the same as that shown in FIG. 11 with the exception that the clamp screw assembly 260 has been removed and replaced with an elevated clamp assembly 360 to hold the implant in a fixed position so that the base 22 is oriented allowing the same to be rounded using rasp 70 shown in FIG. 14. The elevated clamp assembly 360 is mounted in the horizontal grooves 365 cut in the inner side wall 348 of the end sections 234. A thumb screw 366 is threadably mounted on a shaft which is secured to rear clamp bar 354 and extends through intermediate clamp bar 356 and forward clamp bar 358. Rear clamping bar 354 has a knurled top strip 355 to hold base 22 of the meniscus implant in a fixed position so that the bottom can be rounded to fit in groove 202 of tibia 200. As thumb screw 366 is turned, the forward clamp bar 358 and rear clamp bar 354 are pulled together. A matt 353 is secured to the top planar surface 352 of the base section to hold the implant in place as shown for the rasping procedures. The matt 353 can be of knurled construction or a friction surfaced plate which is secured to the base planar surface 352.

Figure 14:
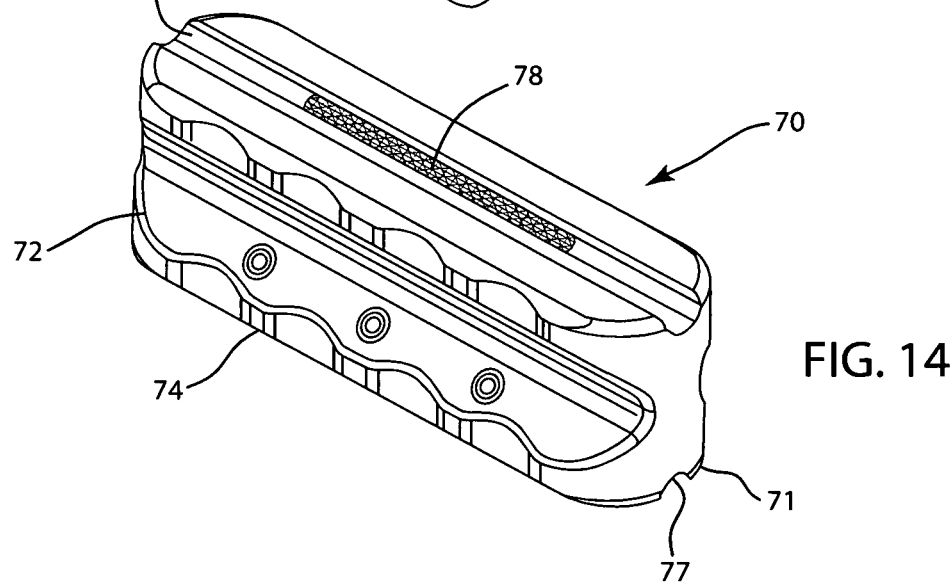
FIG. 14 is a perspective view of an individual graft rasp instrument.

A rasp 70 as shown in FIG. 14 is used to round the meniscus graft base 22 so that the base is formed with a rounded end allowing the same to be fit into groove 202 cut into tibia 200. The rasp 70 has a rounded body 71 with central grip recesses 72 which run longitudinally along its length. The side of the recess defines finger grip indentations 74 and the proximal and distal ends are curved. Grooves 76 and 77 are cut into the body 71 of different widths corresponding to selected widths for the implant base 22 which will be fit into the tibia groove 202. Rasp teeth strips 78 are mounted in grooves 76 and 77 allowing the end of implant base 22 to be rounded to the desired amount. The implant 20 is mounted in clamping assembly 360 in the orientation shown in FIG. 13 prior to having the bottom of the base rounded.

Figure 21:
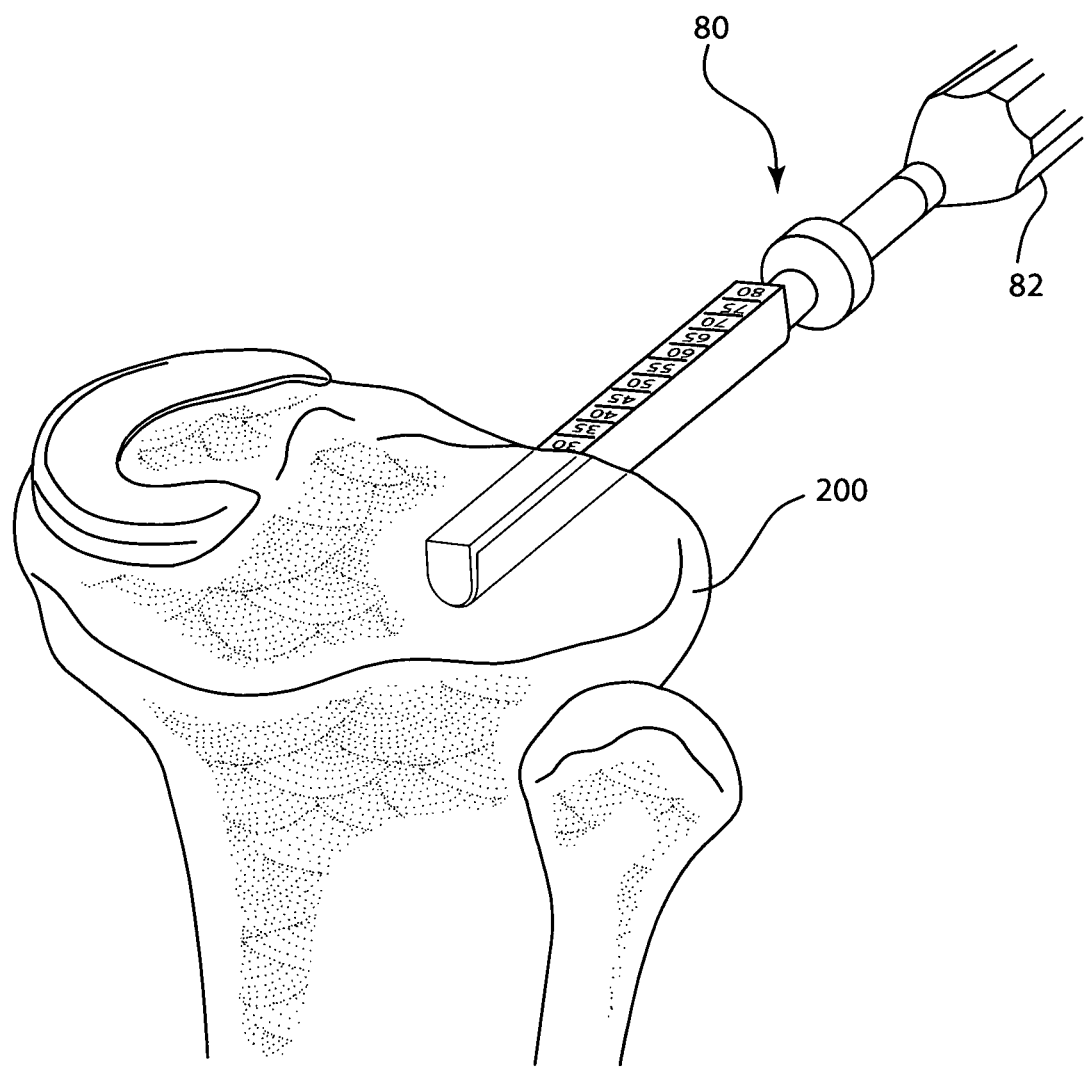
FIG. 21 is a partial top perspective view of the osteotome of FIG. 20 with top measuring indicia showing the handle in phantom section.

An osteotome or tissue chisel 80 as shown in FIGS. 20 and 21 is used to cut the groove 202 of tibia 200 into final shape once the tibia has been drilled to a desired diameter and depth. The osteotome uses a bore cut into the tibia from the drill bit passing over the drill pin as a guide to provide a uniform groove cut as will be later discussed. The tissue chisel/osteotome is constructed with a stainless steel or high impact plastic handle 82 which receives the impact of a hammer via stainless steel striking end member 83. A cutting blade 84 having a predetermined width which corresponds to the width of the base 22 of the implant 20 is mounted to the handle 82 by a solid shaft. The cutting blade 84 has a linear central cutout 86 which runs to the distal end 87 of the cutting blade with a beveled cutting edge 85. The sides of the blade 84 have marking indicia 88 which is printed on the side surface 89 of the blade. The marking indicia may be etched painted or cut into the surface of the blade. This measures the length of the groove 202 in the tibia 200 as the same is being cut.

Figure 22:
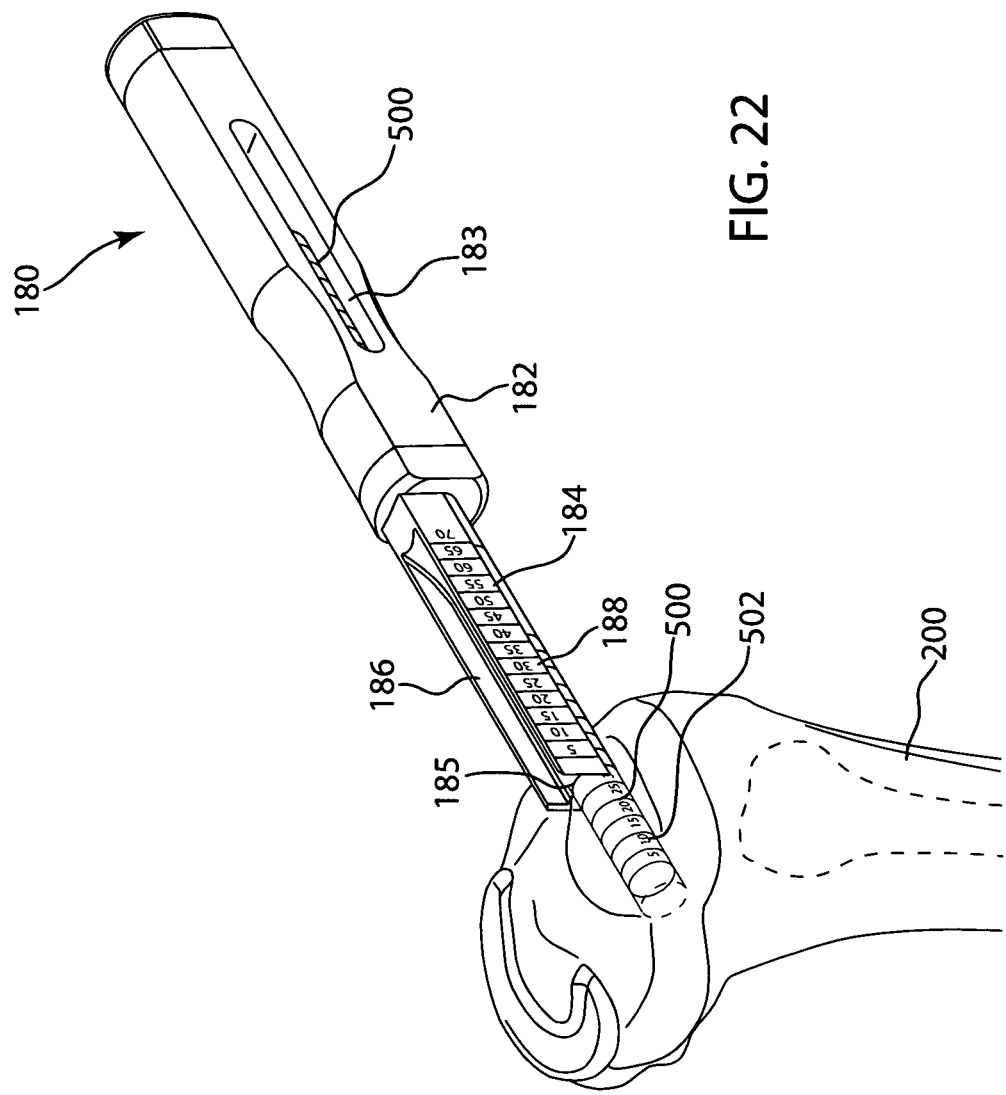
FIG. 22 is a perspective view of an alternate osteotome embodiment with a rod guide and depth mark.
Figure 23:
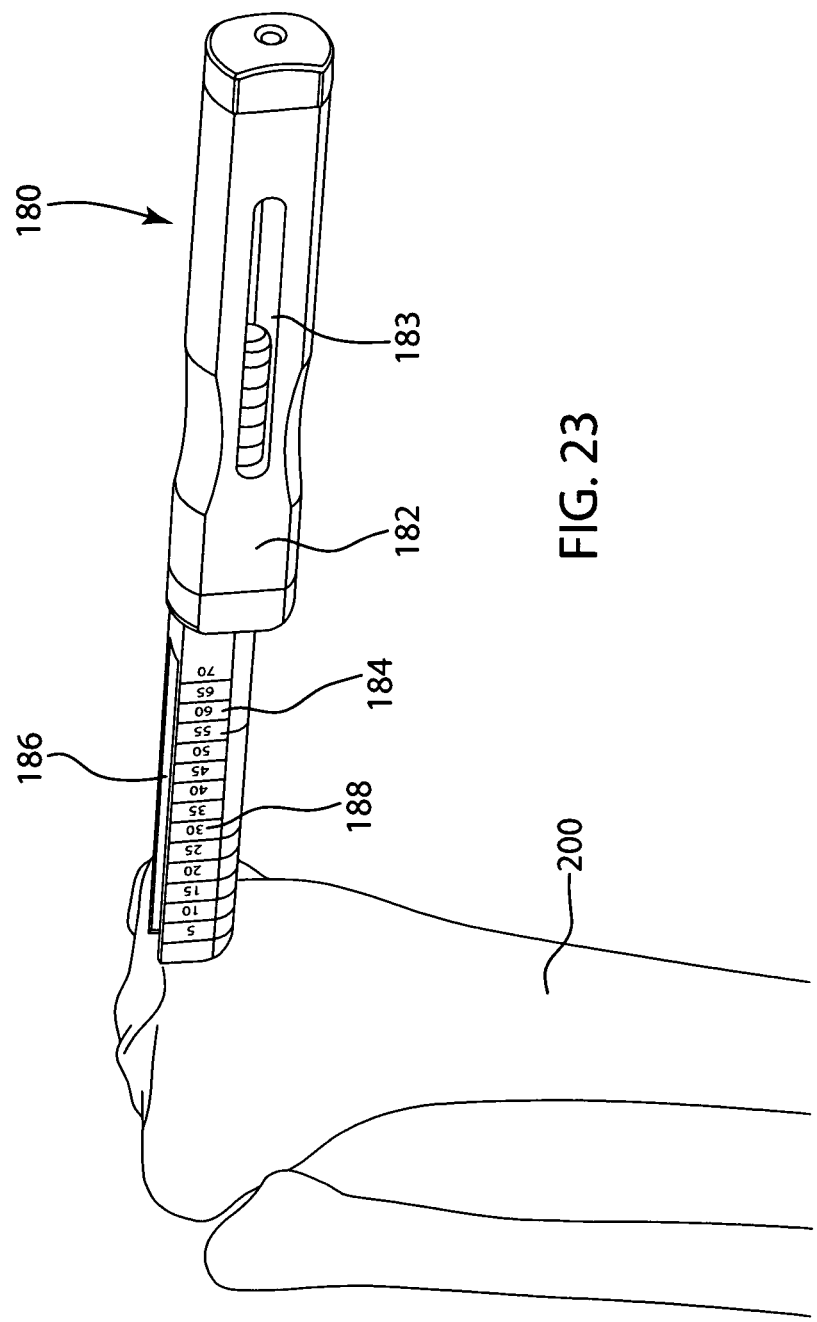
FIG. 23 is a side perspective view of the osteotome with rod guide of FIG. 22.

An alternative embodiment of the osteotome 180 is shown in FIGS. 22 and 23. In this alternate embodiment, a drill hole is drilled around centering guide pin 400. The guide pin 400 preferably has a 2.4 mm diameter. A rod 500 as shown in FIG. 22 is inserted into the drilled hole by the surgeon and the osteotome 180 rides on the rod 500 to provide a uniform groove cut. The rod 500 is preferably provided with depth marking 502. The osteotome 180 rides on the rod 500 by virtue of the semicircle shaped track 185 formed on the bottom of cutting blade 184 to provide a uniform groove cut. A stainless steel handle 182 mounted to cutting blade 184 receives the impact of a hammer to drive blade 184 into the tibia tissue. A slot 183 is cut into the center portion of handle 182 allowing the guide rod 500 and its associated markings 502 to be visualized. The osteotome selected by the surgeon has a cutting blade 184 having a predetermined width which corresponds to the width of the base 122 of the implant. The cutting blade has a linear cutout portion 186 which runs to the distal beveled end of the cutting blade with the sides of the blade having marking indicia 188 printed or etched to allow the surgeon to determine the length of the groove 202 cut into the tibia 200. The marking indicia may be etched, painted or cut into the side surface.

Figure 15A:
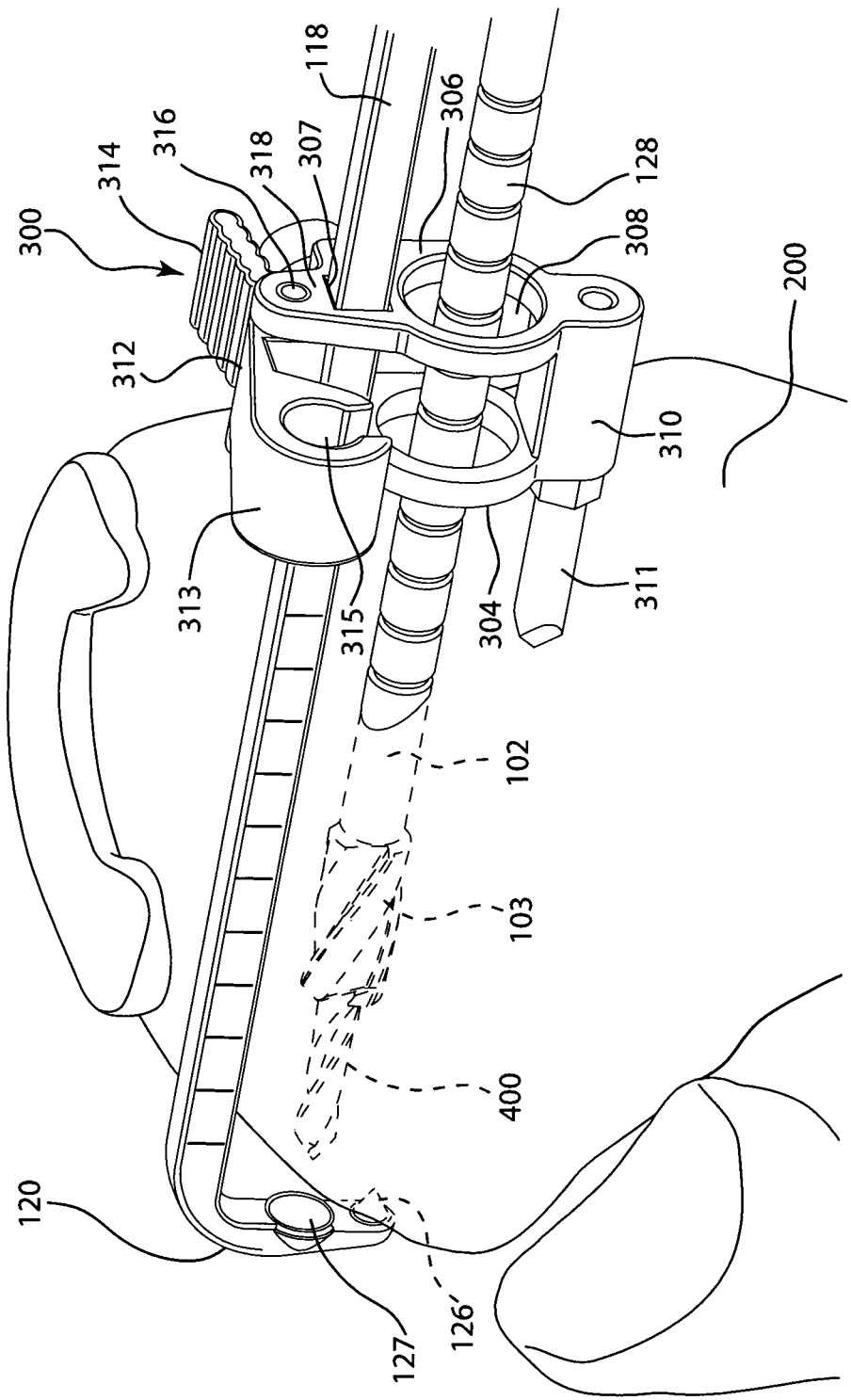
FIG. 15a is a perspective view of a parallel aligner support slide used in the clamping tissue drill shown in FIG. 15.
Figure 15B:
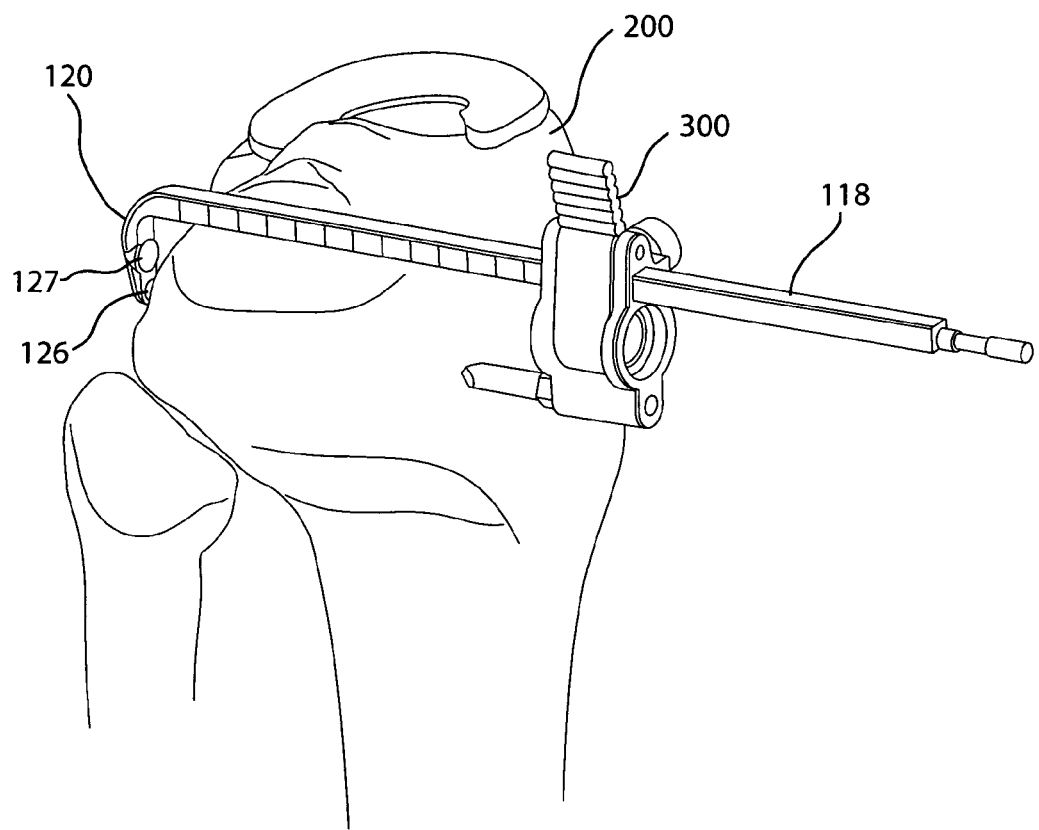
FIG. 15b is an exploded perspective view of the drill removed from the clamp arm and guide rod leaving the same attached to the tibia.
Figure 16:
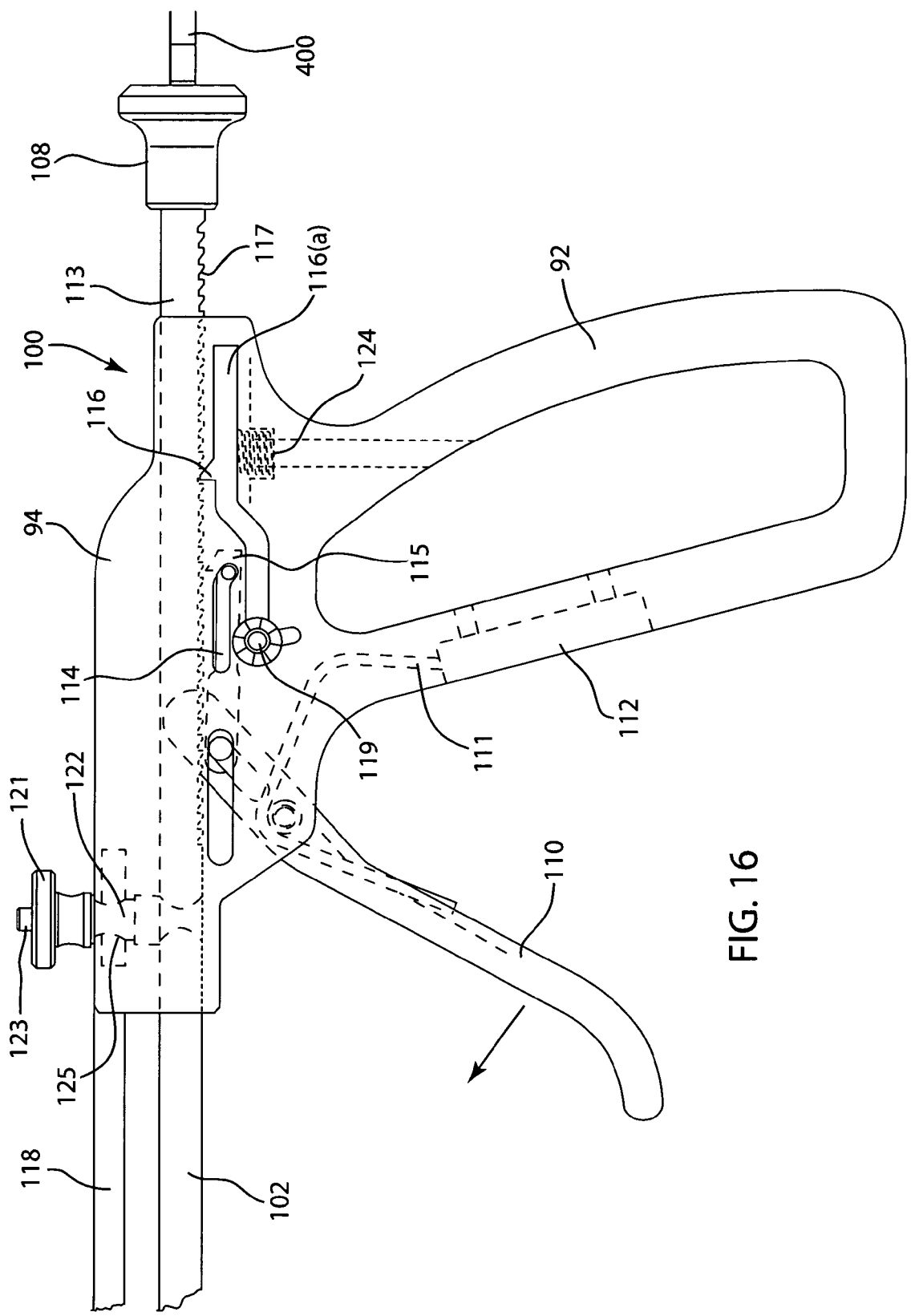
FIG. 16 is an enlarged partial side elevation view of the tissue clamping drill of FIG. 15 showing the drive mechanism in phantom.
Figure 17:
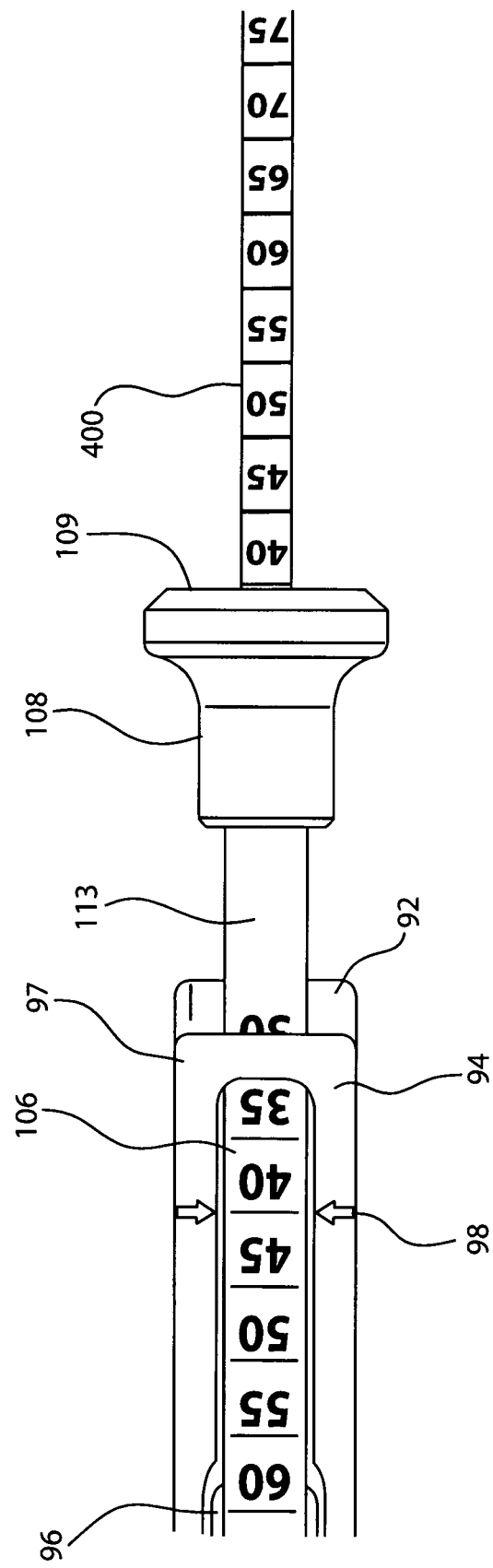
FIG. 17 is an enlarged partial top plan view of the rear of the tissue clamping drill housing of FIG. 15 with a drill depth indicator on the ratchet arm and guide pin.
Figure 18:
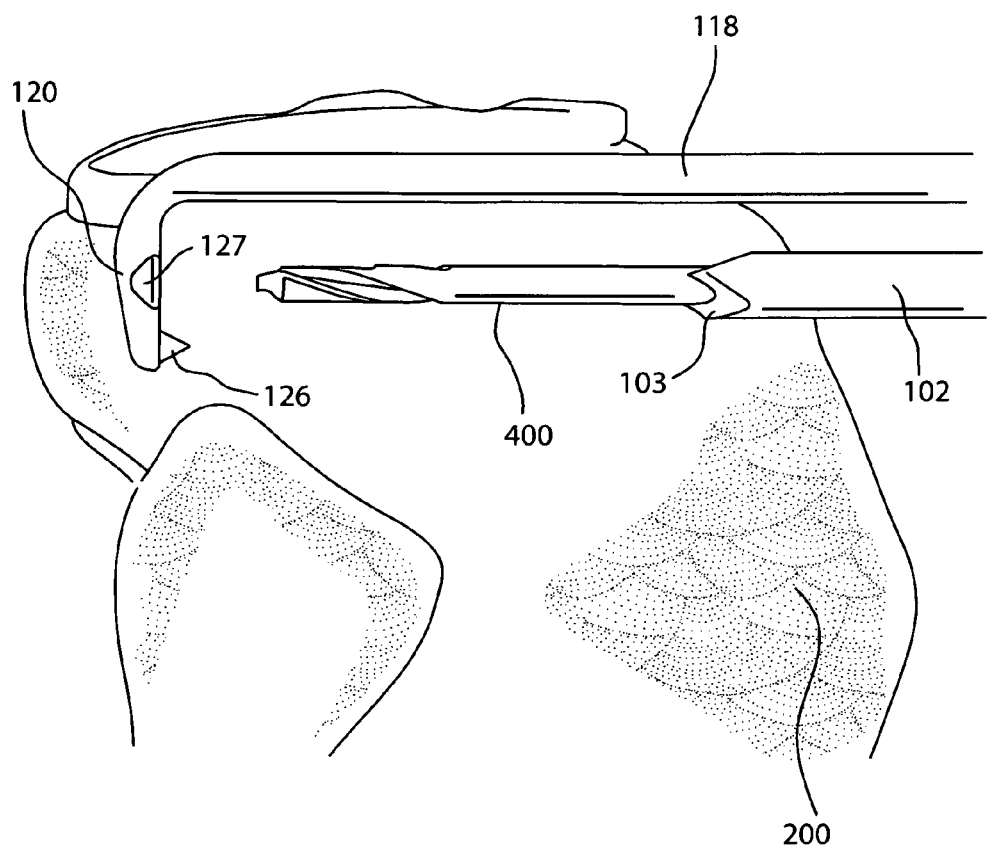
FIG. 18 is an enlarged partial view of the distal end of drill and clamp arm of the tissue clamping drill of FIG. 15 engaging the tibia.

A clamping drill mechanism 90 as shown in FIGS. 15-19 is an instrument utilized in the tibia groove formation. The drill mechanism 90 is constructed with a pistol type grip handle 92 and a drill housing 94 integrally formed with the handle 92. The housing and grip are preferably constructed of titanium but may be constructed of stainless steel. The drill housing 94 defines an open internal chamber 96 which holds the drill bit assembly 100 and drill drive mechanism. The drill bit assembly 100 has a cannulated drill rod or shaft 102 which rides over guide pin 400 with a trocar style cutting bit 103. The drill bit engages the tibia 200 with the drill shaft 102 riding over guide pin 400 which has previously driven into the tibia to drill a bore into the tibia a desired length as shown in FIG. 18. The shaft 102 is marked with indicia 106 as shown in FIG. 15a and FIG. 17 which allows the user to read the depth of penetration of the shaft 102 into the tibia 200 through the opening of chamber 96. The rear section 97 of housing 94 has a marking line 98 as an indicator allowing the surgeon to read the alignment and determine the depth of the drill shaft 102. The proximal end of shaft 102 has a stop member 108 with an end planar surface 109 allowing a reading of the depth marks on the guide pin 400 as can be seen more clearly in FIG. 17.

Figure 19:
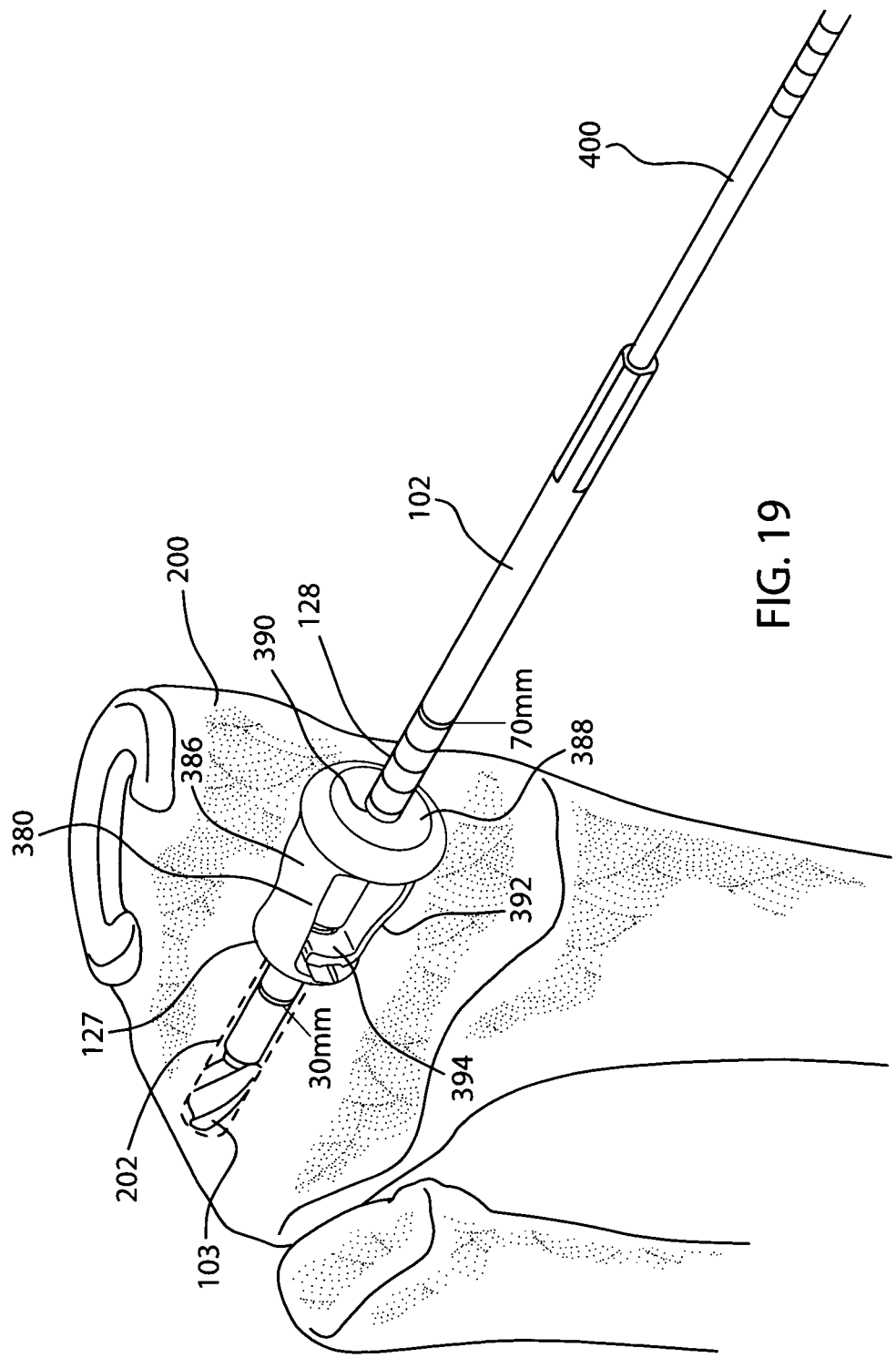
FIG. 19 is an enlarged detailed perspective partial view of the drill bit of the tissue clamping drill with a spring loaded drill stop.
Figure 19A:
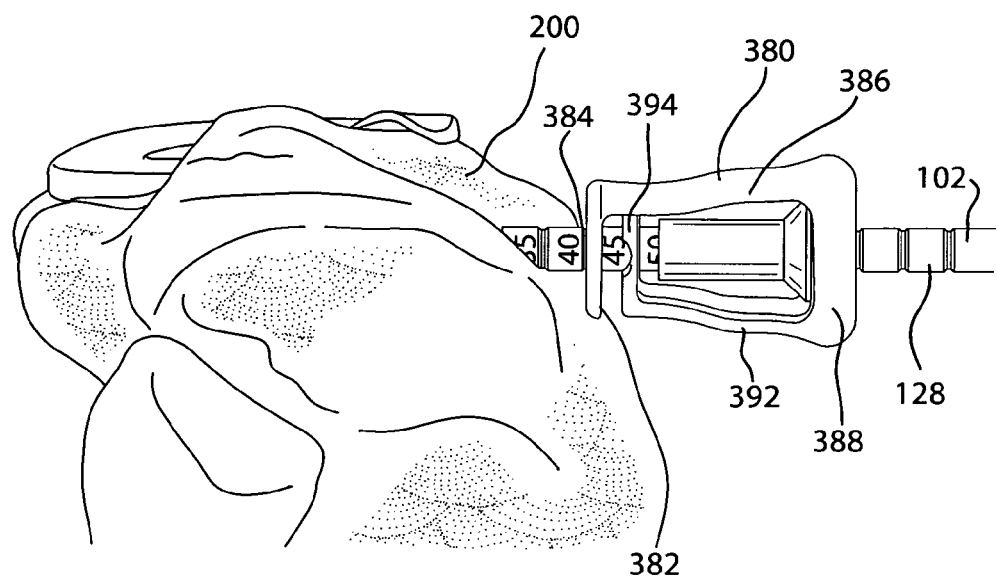
FIG. 19a is an enlarged side elevational view of the drill slot shown in FIG. 19.

If desired, a depth stop collar 380 as shown in FIGS. 19 and 19a can be used by the surgeon. The depth stop collar 380 can be snapped on or off the drill at groove locations 128 cut into the exterior surface of the drill shaft 102. The depth stop collar 380 limits the depth that the drill can penetrate into the tibia.

The drill stop collar 380 snaps on and off the drill at the groove locations 128 which are cut around the circumference of drill shaft 102. The collar 380 is constructed with a front circular member 382 defining an aperture 384 which receives the cannulated drill shaft 102 and an exterior top support strip 386 which is integral with front member 382 and a rounded circular rear member 388. The rear member 388 defines an aperture 390 which receives the cannulated drill shaft 102. A flexible bottom strip 392 is integrally formed with the rear member 388 and has an upwardly turned end member 394 which is spring loaded by the bottom strip 392 to engage and hold the collar in a fixed position in a selected groove 128 cut around the drill shaft 102. When pressure is applied to the top strip 386 and bottom strip 392, end piece 394 is moved outward from shaft 102 to disengage the end member 394 from the groove 128 allowing the stop collar 380 to be moved along the drill shaft 102 to the desired stop measurement.

The drill drive is mounted in drill housing 94 and is best shown in FIG. 16. The drill drive comprises a torsion spring 111 mounted to a spring block 112 secured by pins to the grip handle 92. The torsion spring 111 biases trigger 110 activating a linkage which will engage a ratchet drive to drive the drill shaft 102 forward with each pull of the trigger 110. The trigger 110 is designed to drive the ratchet arm 113 formed at the rear of the drill shaft 102 through the action of linkage 114 and its associated hook member 115, a total of 5 teeth, with each tooth 117 covering a linear distance of 2 mm. The linkage 114 includes a trigger pin which rides in a slot formed in the housing 94, a slide bar mounted to the trigger pin, and a drive hook 115 connected to the slide bar. The limited total forward drive of the drill shaft 102 is a total of 10 mm for each full pull of the trigger 110 which prevents overforce and prevents the cortical covering of the tibia from being cracked. Thus, each click (one tooth) of the trigger will drive the ratchet arm 113 and its associated drill shaft 102 over the pawl 116, a distance of 2 mm. Once the trigger 110 has been pulled to its furtherest extent, release pin 119 is engaged and pulled downward driving the pawl arm 116(a) against spring 124 so that pawl 116 and its biased arm 116(a) is disengaged from the teeth 117 of the ratchet arm 113 of the drill shaft 102. As pawl 116 and drive hook 115 are biased downward from engagement with ratchet arm 113, the trigger 110 is returned by spring 111 to its forward position. The pawl mechanism 116(a) is continuously urged upward against the ratchet arm 113 by the expansion of coil spring 124. The rear section of shaft 102 forming the ratchet arm 113 has a circular stop 108 mounted thereto which limits the maximum forward movement of the drill shaft 102.

A locking mechanism 121 in the form of a threaded thumb lock with a channeled base 125 is mounted on a threaded shaft 123 and is adapted to engage the fixed clamp arm 118 to hold the same in a fixed clamped position. The clamp arm 118 is mounted to the housing 94 above the drill bit assembly 100. The removable clamp arm 118 has an angled distal end section 120. The end section 120 is formed with an inwardly projecting sharp conical point 126 for engaging the tibia and defines a drill detaining cup 127 which limits drill advancement so that the drill does not enter tissue and cut through blood vessels, nerves or tissue.

A parallel aligner mechanism 300 as shown in FIGS. 15 and 15(a) is mounted on the drill shaft 102 and the clamp arm 118 which keeps the shaft 102 and clamp arm 118 from bending from the stress created during the clamping drilling process. The aligner body 302 has two parallel arms 304 and 306, each of which defines a square aperture 307 through which clamp arm 118 extends which allows the body 302 to be slid along clamp arm 118. Each arm 304/306 defines a second circular aperture 308 through which the drill shaft 102 is inserted. The bottom of the body defines a spacer pin assembly 310 which is secured to both arms. The spacer pin assembly has an extending pin member 311 which engages the tibia. A rotatable cam member 312 with a thumb extension 314 is rotatably mounted over pin 316 which is mounted in the upper section 318 of each arm 304/306. When the thumb extension 314 is moved upward, it is cammed onto the clamp arm 118 holding the aligner mechanism 300 in a fixed position with the "C" shaped end member 313 being rotated over shaft 102. Shaft 102 is slideably mounted in circular channel 315 of end member 313. The thumb piece 314 is positioned upright forming a guide as seen in FIG. 15.

After the drill has been used and a blind bore formed in the tibia, the drill shaft 102 is removed and an optional centering rod 500 may inserted into the bore cut by the drill so that the osteotome 180 is positioned for a uniform cut as to depth and length. If no centering rod is used, osteotome 80 is used to cut the groove 202.

In operation the implant 20 has its bone base 22 cut to a desired height and width in workstation 30/130/230. The finished implant base 22 is measured in the appropriate sizing groove 37 of the workstation for width and length. A guide pin 400 is inserted through the thin cortical shell of the tibia 200 into the soft cancellous portion at a depth which will allow the appropriate length of groove 202 to be cut into the tibia 200. The guide pin 400 does not engage the cortical shell on the opposite side of the tibia. The guide pin 400 is provided with depth marker indicia at one end. The drill shaft 102 is mounted over the guide pin 400 with the guide pin seated in the cannula of the drill shaft. The tibia 200 is then drilled with drill shaft 102 inserted to the appropriate depth and length by triggering the ratchet drive driving the shaft 102 forward. The drill shaft is removed leaving a blind bore in the tibia 200. As previously noted, a rod 500 may be inserted into the drilled blind bore with a friction fit. If rod 500 is not used, the osteotome or tissue chisel 80 is positioned adjacent the bore and pushed forward by the surgeon to cut a groove 202 in the cancellous bone of the tibia. The groove 202 is formed in the tibia with the osteotome 80 so that the width is the same as the width of the implant bone base 22 with the end 204 of the groove 202 stopping about 5 mm from the posterior wall 206 of the tibia. Because of the natural slope of the tibia from the posterior wall 206 to the anterior wall 208 is about 5° to about 10°, the groove 202 does not run across the entire upper surface of the tibia as seen in FIG. 24. The bone base 22 having been trimmed to the correct width and height in the workstation 30/130/230 by making desired vertical and horizontal cuts is rasped to have a rounded end and is press fit into the cancellous bone tibia groove 202. If desired, the implant may be secured with a bone screw depending upon the patient and the desire of the surgeon. The center height of the bone base is constant with a 7 mm width having a height of 9.5 mm; a 8 mm width having a 10 mm height; a 9 mm width having a 10.5 mm height and an 11 mm width having an 11 mm height. It should be noted that an abutment shoulder or end portion 204 is formed at the end of groove 202 to seat the implant bone base 22 in a fixed position and the distance from the cortical bone layer on the tibia keeps the osteotome blade from shattering the thin cortical bone layer on the tibia.

The principles, preferred embodiments and modes of operation of the present invention have been described in the foregoing specification. However, the invention should not be construed as limited to the particular embodiments which have been described above. Instead, the embodiments described here should be regarded as illustrative rather than restrictive. Variations and changes may be made by others without departing from the scope of the present invention as defined by the following claims:

What we claim is:

1. A kit for placing an allograft meniscus implant on the surface of a human tibia comprising a meniscal implant of allograft material including a bone base and instrumentation comprising; (a) a drill apparatus, (b) an osteotome, and (c) a cutting workstation, said cutting workstation comprising an integral U shaped housing having a base with a planar bottom surface and integral end sections extending away from said base, each of said end sections being formed with a planar end wall and planar side walls, a groove formed on a side wall of each end section and fastening means mounted to a cutting guide bar slideably seated in each side wall groove holding said cutting guide bar to said side walls allowing said cutting guide bar to assume a selected orientation from a plurality of angular orientations with respect to said housing base planar surface said cutting guide bar being moveably mounted on said housing and adapted to fixedly mounted on said housing to assume an angular position, said cutting guide bar defining a throughgoing cutting slit, an implant clamping assembly, said implant clamping assembly comprising a clamping support bar mounted to said housing, and a clamping mechanism mounted to said clamping support bar, said clamping mechanism including a thumb screw threadably mounted to said clamping support bar, said clamping mechanism being adapted to be extended into said housing to engage and hold a transplant in place.

2. A kit as claimed in claim 1 wherein each housing end section is substantially rectangular in configuration and defines a plurality of parallel grooves of different widths, each of said grooves defining a rounded bottom.

3. A kit as claimed in claim 1 wherein said cutting workstation clamping support bar has a centrally positioned inclined surface section upon which said clamping mechanism is mounted.

4. A kit as claimed in claim 1 wherein said cutting workstation clamping support bar is mounted in recess seats formed in said end sections.

5. A kit as claimed in claim 1 wherein said cutting workstation has a drop in insert mounted to said end sections, each of said end sections having a planar inside end wall which defines a groove having a width which will hold said drop in insert, said drop in insert comprising a bar with a longitudinal linear slit cut there through adapted to receive a cutting blade for trimming said implant.

6. A kit as claimed in claim 1 wherein said drill apparatus comprises a housing with an integral pistol type grip handle, a trigger assembly moveably mounted to said housing, a spring mounted to said housing biasing said trigger assembly, a cannulated drill shaft mounted in said housing, said drill shaft being driven forward by drive means mounted in said housing activated by pulling said trigger assembly and a clamping rod mounted in said housing and extending past said shaft, said clamping rod having an angular end section which extends at an angle from an axis of said rod with means mounted on the end of said angular end section for engagement of a tibia surface.

7. A kit as claimed in claim 6 wherein said cannulated drill shaft is sized to receive a guide pin, said drill shaft defining a ratchet formed on at least a section of its surface and a stop member mounted on said drill shaft's proximal end.

8. A kit as claimed in claim 6 wherein said drill shaft has depth marking indicia placed upon at least a portion of its surface.

9. A kit as claimed in claim 6 wherein said drive means comprises drive linkage slideably mounted to said housing and connected to said trigger assembly, said drive linkage including a hook engaging member which engages a ratchet section formed on said drill shaft and pulls said ratchet section and drill shaft forward upon the activation of said trigger.

10. A kit as claimed in claim 9, wherein said ratchet section is pulled forward by the movement of said trigger a maximum of 10 mm.

11. A kit as claimed in claim 6 wherein said drill apparatus housing has a spring activated pawl member mounted thereto, said pawl member defining a pawl arm with a pawl which engages a ratchet section to limit movement of said ratchet section in one direction and a release mechanism to move said pawl away from said ratchet.

12. A kit as claimed in claim 6 wherein said clamping rod angular end section has a conical member projecting back towards said housing, said angular end section also defining a cup adapted to limit the forward movement of said drill shaft.

13. A kit as claimed in claim 6 wherein said drill shaft is formed with a ratchet section, drive means is moveably mounted in said housing connecting said trigger to said ratchet section to drive said ratchet section forward when said trigger is rotated, and a pawl mounted in said housing, said pawl being biased against said ratchet to limit movement of said drill shaft to one direction.

14. A kit as claimed in claim 1 including a rasp.

15. A kit as claimed in claim 1 wherein said osteotome comprises a cutting blade mounted to a striking handle, said cutting blade defining a linear cutout portion which runs to the distal end of said cutting blade, the distal end of said cutting blade being beveled with the sides of said blade having marking indicia representing a linear distance placed on a side surface of said cutting block.

16. A kit as claimed in claim 1 wherein said osteotome comprises a cutting blade mounted to a striking handle, said cutting blade defining a linear cutout portion which runs to the distal end of said cutting blade; the distal end of said cutting blade being beveled with the sides of said blade having marking indicia representing a linear distance placed on a side surface of said cutting block, said cutting blade defining a curved channel on its bottom surface, said curved channel being adapted to be mounted on a rod.

17. A kit for placing an allograft meniscus implant on the surface of a human tibia comprising a meniscal implant of allograft material including a bone base and instrumentation comprising; (a) a drill apparatus having a housing with an integral pistol type grip handle extending from said housing, a trigger assembly moveably mounted to said housing, a cannulated drill shaft mounted in said housing, said drill shaft being driven by drive means mounted in said housing activated by pulling said trigger assembly and a clamping rod mounted in said housing and extending past said drill shaft, said clamping rod having an angular end section with a member mounted on the end of said angular end section projecting back towards said housing, (b) a osteotome comprising a cutting blade mounted to a striking handle, said cutting blade defining a linear cutout portion which runs to the distal end of said cutting blade, the distal end of said cutting blade being beveled with the sides of said blade having marking indicia representing a linear distance placed on a side surface of said cutting block, and (c) a cutting workstation comprising a housing defining a base with a planar bottom surface and integral end sections extending away from said base, each of said end sections being formed with a planar end wall and planar side walls, a groove formed on a side wall of each end section and fastening means mounted on opposing ends of a cutting guide bar, said fastening means being moveably seated in each side wall end section groove, said cutting guide bar being slideably mounted along each said side wall groove with each opposing end of said cutting guide bar being able to be independently moved a desired distance from said housing base planar bottom surface allowing said cutting guide bar to assume a plurality of angular orientations with respect to said cutting workstation housing base planar bottom surface, and clamping means mounted on said cutting workstation housing, said clamping means being adapted to engage said meniscal implant and hold it in a fixed position.

* * * * *